(12) United States Patent
Leu et al.

(10) Patent No.: US 6,194,210 B1
(45) Date of Patent: Feb. 27, 2001

(54) HEPATITIS A VIRUS CULTURE PROCESS

(75) Inventors: Frank S. Leu, Lansdale; Douglas B. Seifert, Hatfield, both of PA (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/634,011

(22) Filed: Apr. 17, 1996

Related U.S. Application Data

(63) Continuation of application No. 08/208,162, filed on Mar. 8, 1994, now abandoned.

(51) Int. Cl.[7] .............................. C12N 5/00; C12N 5/02; C12N 7/01; A61K 39/29
(52) U.S. Cl. ............ 435/403; 435/669.3; 435/235.1; 435/239; 435/383; 435/394; 435/455; 435/456; 424/226.1
(58) Field of Search ..................... 435/235.1, 69.3, 435/239, 383, 394, 403; 424/226.1

(56) References Cited

U.S. PATENT DOCUMENTS

| | | | |
|---|---|---|---|
| 3,105,011 | 9/1963 | Mclean et al. | 424/226.1 |
| 3,976,547 | 8/1976 | McAleer et al. | 435/299.1 |
| 3,994,870 | 11/1976 | Neurath et al. | 530/380 |
| 4,017,601 | 4/1977 | Hilleman et al. | 424/226.1 |
| 4,029,764 | 6/1977 | Provost et al. | 424/226.1 |
| 4,031,203 | 6/1977 | Provost et al. | 424/226.1 |
| 4,164,566 | 8/1979 | Provost et al. | 424/226.1 |
| 4,275,165 | 6/1981 | Lorenz et al. | 435/235.1 |
| 4,296,204 | 10/1981 | Grabner et al. | 435/235.1 |
| 4,301,249 * | 11/1981 | Markus et al. | 435/235.1 |
| 4,324,861 * | 4/1982 | Kun | 435/237 |
| 4,412,002 | 10/1983 | McAleer et al. | 435/237 |
| 4,415,670 | 11/1983 | Grabner et al. | 435/259 |
| 4,448,884 | 5/1984 | Henderson | 435/402 |
| 4,506,016 | 3/1985 | Flehmig | 435/237 |
| 4,532,215 | 7/1985 | Daemer et al. | 435/237 |
| 4,564,532 | 1/1986 | Henderson | 427/2.1 |
| 4,594,339 * | 6/1986 | Lopez et al. | 514/42 |
| 4,605,623 | 8/1986 | Malette et al. | 435/377 |
| 4,614,793 | 9/1986 | Hughes et al. | 530/350 |
| 4,620,978 | 11/1986 | Daemer et al. | 424/226.1 |
| 4,636,385 * | 1/1987 | Plotkin et al. | 424/215.1 |
| 4,636,469 | 1/1987 | Daemer et al. | 435/237 |
| 4,683,294 | 7/1987 | Van Wijnendaele et al. | 530/371 |
| 4,721,675 * | 1/1988 | Chan et al. | 935/239 |
| 4,783,407 | 11/1988 | Provost et al. | 435/235.1 |
| 4,894,228 | 1/1990 | Purcell et al. | 424/129.1 |
| 4,963,489 | 10/1990 | Naughton et al. | 435/1.1 |
| 4,975,377 | 12/1990 | Kay | 435/297.5 |
| 5,004,688 | 4/1991 | Craig et al. | 435/69.3 |
| 5,021,348 | 6/1991 | Giesa et al. | 435/237 |
| 5,151,023 | 9/1992 | Kuzuhara et al. | 424/202.1 |
| 5,160,490 | 11/1992 | Naughton et al. | 435/287.1 |
| 5,268,292 | 12/1993 | Robertson et al. | 435/239 |

FOREIGN PATENT DOCUMENTS

| | | |
|---|---|---|
| 1 196 590 | 11/1985 | (CA) . |
| 0 025 745 | 3/1981 | (EP) . |
| 0 044 793 | 1/1982 | (EP) . |
| 0 199 480 | 10/1986 | (EP) . |
| 0 302 692 | 8/1989 | (EP) . |
| 0 339 667 | 11/1989 | (EP) . |
| 0 339 668 | 11/1989 | (EP) . |
| 0 413 637A1 | 2/1991 | (EP) . |
| 0 468 702A2 | 1/1992 | (EP) . |
| 0 583 142 A2 | 2/1994 | (EP) . |
| 7723372 | 2/1979 | (FR) . |
| 01279843 | 11/1989 | (JP) . |
| 85/01517 | 4/1985 | (WO) . |
| 88/00973 | 2/1988 | (WO) . |
| 89/00097 | 1/1989 | (WO) . |
| WO 94/06446 | 3/1994 | (WO) . |
| PCT/US95/ 02516 | 6/1995 | (WO) . |

OTHER PUBLICATIONS

Feinstone, et al., J. Vir. 13, No. 6 p. 1412–1414 (1974).
Feinstone, et al., Science, 182, p. 1026–1028 (1973).
Bradley, et al., Iso. Char. of Hep. A Virus p. 876–889 (1976).
Gaus–Muller, et al., J. Med. Virol. 7, p. 233–239 (1981).
Siegl, et al. J Virol. p. 40–47 (1978).
Provost, et al., J. Med. Virol. 20, p. 165–175 (1986).
Mascoli, et al., PSEBM 142, p. 276 (1973).
Flehmig, et al., Viral Hep. and Liver Disease 87–90 (1988).
Flehmig, et al., Viral Hep. and Liver Disease 100–105 (1988).

(List continued on next page.)

Primary Examiner—Marianne P. Allen
Assistant Examiner—Mary K. Zeman
(74) Attorney, Agent, or Firm—Anna L. Cocuzzo; Joanne M. Giesser; Jack L. Tribble

(57) ABSTRACT

A microcarrier based process to produce viral vaccines, of which one example is hepatitis A virus (HAV), is composed of an aggregated microcarrier system of glass coated polystyrene microcarriers and MRC-5 cells which creates a stable environment for the propagation of the virus over even extended infection periods. The microcarrier aggregates formed according to this process eliminate the sloughing of cells from the beads during long cultivations seen in other systems, allowing high virus productivity in microcarrier culture. The methodology is applicable where virus production can be enhanced by creating a stable culture during an extended infection period. Scalable stirred bioreactors are used instead of multiple parallel stationary surface bioreactors. This aggregated microcarrier process eliminates the capacity limitations of stationary surface bioreactors, it protects the cells upon which virus is cultured from shear, it provides enhanced cell to cell interactions, it provides a stable environment for virus growth, it provides void space for the convective transport of nutrients through the aggregate, and it provides a straight forward method for harvesting the viral lysate for downstream processing.

12 Claims, 20 Drawing Sheets

OTHER PUBLICATIONS

Flehmig, et al., J. Med. Virol., 22, 7–16 (1987).
Kusov, et al., Vaccine, 5(8) p. 540–541, Aug. (1991).
Andre, et al., Prog. Med. Virol. Basel, Karger, 37, p. 72–95 (1990).
Jacobson, Wall Street Journal, p. B1 & B6 Aug. 13, 1992.
Werzberger, et al., Abstracts of the American Pediatric Society, p. 103A abstr. #601 (Jun., 1992).
Bancroft, New Eng. J. of Med. 327 p. 488–490 (1992).
Werzberger, et al., New Eng. J. of Med. 327, No. 7, p. 453–457 (1992).
Coulepis, et al., Intervirology 10, p. 24–31 (1978).
Coulepis, et al., Chemical Abstracts, 88, p. 226 (1978).
Costar—Product Description for the Cellcube (1991).
Hurni & Miller, J. of Chrom. 559, p. 337–343 (1991).
Iino, et al., Vaccine, 10, p. 5–10 (1992).
Wood & Minor, Biologicals 18, p. 143–146 (1990).
Mann, Develop. Biol. Standard, 37, p. 149–152 (1977).
Wheeler, Cosette, et al., J. of Clin. Microbiol. 23, No. 3, p. 434–440 (1986).
Johnston, et al., J. Infec. Diseases, 157, No. 6, p. 1203–1211 (1988).
Robertson, et al., J. Gen. Virol. 69, p. 2129–2134 (1988).
Scholz, et al., J. of Virol., 70, p. 2481–2485 (1989).
Einberger, et al., J. of Virol., 64, No. 9, p. 4274–4280 (1990).
Hughes, et al., J. of Virol., 52, No. 2, p. 465–473 (1984).
Philipson, Methods in Virol., II, p. 235–244 (1967).
Lewis, et al., Proc. of Int. Symp. on Viral Hep. and Liver Disease p 94–97 (1990).
Provost, et al., Int. Symp. on Viral Hep. and Liver Disease p 83–84 (1988).
Hilleman, et al., Viral Hep. Int'l. Symp. p. 385–397 (1981).
Rueckert & Pallansch, Methods in Enzymal, 78, p. 315–325 (1981).
Kerr & Martin, J. of Virol., 9, p. 559–561 (1972).
Provost, et al., Soc. for Exp. Bio. & Med., 170, p. 8–14 (1982).
Provost, et al., J. of Med. Virol., 19, p. 23–31 (1986).
Provost, & Hilleman, Soc. for Exp. Bio. & Med., 160, p. 213–221 (1979).
Siegl, et al., Intervirology, 22, 218–226 (1984).
Hughes, et al., J. of Virol. 52, No. 2, p. 465–473 (1984).
Wheeler, et al., J. of Virol., 58, No. 2, p. 307–313 (1986).
Ticehurst, Seminars in Liver Disease, 6, No. 1 p. 46–54 (1986).
Mijch & Gust, Seminars in Liver Disease, 6, No. 1, p. 42–45 (1986).
Hornbeck, et al., Intervirology, 6, p. 309–314 1976.
Locarnini, et al., Intervirology, 10, p. 300–308 (1978).
Siegl & Frosner, J. of Virol., 26, p. 40–47 (1978).
Siegl et al., J. Gen. Virol., 57, p. 331–334 (1981).
Najarian, et al., Proc. Natl. Acad. Sci., USA, 82, p. 2627–2631 (1985).
Gerety, in Gerety (Ed.) Hep. A, p. 263–276 (1984).
Feinstone, Progress in Liver Diseases, VIII, p. 299–310 (1986).
Maniatis, et al., Molecular Cloning, Cold Spring Harbor, p. 458 & 80 (1970).
Divizia, et al., Microbiologica, 9, p. 269–278 (1986).
Cromeans, et al., Viral Hep. and Liver Disease, p. 24–26 (1988).
Divizia, et al., Viral Hep. and Liver Disease, p. 27–30 (1988).
Provost, in Hepatitis A, Gerety Ed., p. 245–261 (1984).
Provost & Hilleman, Soc. for Exp. Bio. and Med., 159, p. 201–203 (1978).
Zachoval, et al., in Hepatitis A, Gerety Ed., p. 33–46 (1984).
ATCC, Cell Lines and Hybridomas, Certified Cell Lines – CCL, p. 43–45, 98 & 101, (7th Ed. (1992).
M. Mutsakis et al., Chem. Eng. Prog., p. 41–48 (Jul. 1986).
M. Mutsakis et al., Water Eng. & Mgmt., Static mixers bring benefits to water/wastewater operations (Nov. 1986).
M. Mutsakis, Sulzer Tech. Rev., 87, p. 108–114 (Mar. 1977).
M. Mutsakis et al., Nature, 244, p. 353–354 (Aug. 1973).
S. D. Perry et al., Biotechnology & Bioengineering, 34, p. 1–9 (Jun. 1989).
J. Epstein et al., In Vitro Cell. & Dev. Biol., 25 No. 2, (Feb. 1989).
J. A. Friberg, In Vitro Cell. Dev. Biol., 28A, p. 215–217 (Mar. 1992).
A. Harris, Exptl Cell Res., 77, p. 285–297 (1973).
E.R. McKillip et al., Bio/technology, p. 805–810 (Sep. 1991).
P. C. Familletti et al., Bio/Technology, 6, p. 41–43 (Jan. 1988).
S. Mitsuda et al., J. of Ferm. & Bioengineering, 70, No. 4, p. 289–291 (1990).
S. M. Edgington, Bio/Technology, 10, p. 855–860 (Aug. 1992).
Hughes & Stanton, J. Virol., 55, No. 2, p. 395–401 (Aug. 1985).
J de Chastonay & G. Siegl J. Virol., 157, p. 268–275 (1987).
W. R. Tolbert et al., In Vitro,. 16(6); p. 486–490 (1980).
M. C. Borys & E. T Papoutskis, Cytoechnology,. 8; p. 347–248 (1992).
S. Goetghebeur & W.–S. Hu, Appl. Microbiol. Biotechnol. 34; p. 735–751 (1991).
J. Varani et al., Biotechn. & Bioeng., XXV; p. 1359–1372 (1983).
A. Widell et al., J. Virol Meth., 8; p. 63–71, (1984).
B. H. Junker et al., Cytotechnology, 9; p. 173–187 (1992).
Junker et al, Cytotechnology, 9: 173–817, 1992.*
Varani et al, J. Biol. Stand., 13: 67–76, 1985.*
Peetermans, Vaccine, vol. 10, Suppl. 1, S99–S101, 1992.*
Griffiths et al "Cell Biology: Experimental Aspects" in *Animal Cell Biotechnology* vol. 1 Spier et al Eds, Academic Press London 1985 pp 50–83.*
Van Wezel et al "Monolayer Growth Systems: Homogeneous Unit Processes" in *Animal Cell Biotechnology* vol. 1 Spier et al Eds Academic Press London 1985 pp 265–282.*
Salk et al, "Noninfectious Poliovirus Vaccine" in *Vaccines* Plotkin et al Eds W.B. Saunders Co. Phila PA 1988 pp158–181.*
Takahashi T, "Varicella Vaccine" in *Vaccines,* Plotkin et al Eds, W.B. Saunders Co. Phila PA 1988 pp526–548.*
Preblud et al, "Measles Vaccine" in *Vaccines* Plotkin et al Eds. W.B. Saunders Co. Phila PA 1988 pp 182–222.*
Dawson et al *Data For Biochemical Research* Claren et al Press Oxford $3^{rd}$ Ed. 1986 pp. 288–289.*

Varani et al, J. Biol. Stand. 13:67–76, 1985.*
Giard et al, Appl Environ Microbiol 34(6):668–72, 1977.*
Varani et al, J. Biol Stand 14:331–336, 1986.*
Nilsson K, Biotechnology & Genetic Engineering Reviews 6:403–439, 1988.*

Thilly et al Methods in Enzymology, 58 184–194, 1979.*
Plotkin S.A. "Rubella Vaccine" in *Vaccines,* Plotkin et al Eds, W.B. Saunders Co. Phila PA 1988 pp235–262.*

* cited by examiner

HEPATITIS A VIRUS CULTURE PROCESS

This is a continuation of Ser. No. 08/208,162 filed on Mar. 8, 1994.

BACKGROUND OF THE INVENTION i. Field of the Invention

The field of this invention is a process for the production of viruses in microcarrier cell culture. Perfused MRC-5 cells cultured on glass-coated microcarriers and infected with hepatitis A virus exemplifies the process.

ii. Background

Many viruses and therapeutic proteins are produced by anchorage dependent cells where cell attachment to a surface is a prerequisite for cell growth and proper function of the cell line. When relatively small quantities are required, multiple T-flasks and Roller bottles have been traditionally used to supply the required surface area. Other commercially available systems such as NUNC CELL FACTORIES cell culture system and COSTAR CUBES cell culture system have substantially increased surface area and thus increased productivity per bioreactor unit. However, these systems still require multiple bioreactor units for large quantities and are therefore limited in scale-up potential for commercial production.

Various packed bed systems have also been developed, including hollow fiber reactors, packed beds of spheres, packed beds of randomly oriented fibers, and porous ceramic monoliths. These systems have documented difficulties with maintaining nutrient supply to the cells in the reactor due to the reactor configuration and restrictions of nutrient transport paths due to cell growth. Hollow fiber reactors rely on diffusion and Starling flow to supply medium flow across the cell compartment [see J. M. Piret (1989), B.c.D Thesis, Dept. of Chem. Eng., Mass. Inst. Technology, August 1989]. Diffusive nutrient penetration is only adequate if the depth of the cell accumulation on the fibers is controllable and uniform, which it is not in these reactors. Starling flow decreases as cell growth occurs, due to increased flow resistance offered by the cell growth. This reduces mixing within the cell growth chamber. Randomly packed beds of beads or fibers rely on forced convection, and are both prone to channeling through paths of least hydraulic resistance, bypassing the areas where surface area is most dense, and hence likely to contain cells. Porous ceramic monoliths are better in this respect, but these suffer from the second factor, biofouling. As the cells grow on the attachment surface, they can constrict and occlude the paths where medium flow occurs [J. E. Putnam et al., Ann. Mtg. Soc. Ind. Microbiol., Orlando, Fla., Aug. 1, 1990]. In the case of the ceramic monolith, cell growth results in restriction of the channel, such that increased hydraulic resistance to flow is offered. The medium then preferentially flows to other parallel channels, and the result is that the channel with the heaviest cell growth receives the least medium. Due to these heterogeneities in the cellular microenvironment and limited scale-up potential, these reactors have had limited success; no U.S. licensed human vaccines or therapeutics are known to be produced in these systems.

The use of solid static mixer elements in cell and virus culture is known, see Grabner and Paul, U.S. Pat. No. 4,296,204. The use of a mesh for culturing primary tissues comprised of several cell types is found in U.S. Pat. No. 4,963,489 and 5,160,490. The tissue resulting from a mesh culture of stromal fibroblasts is claimed in U.S. Pat. No. 4,963,489. Using motionless mixing elements as the surface for cell growth provides uniform nutrient transport to the cell population. The scale-up, cleaning, and sterilization issues remain a challenge for commercial application of these bioreactor systems. In addition, the biomass in these systems cannot be directly monitored during the cultivation. Therefore, indirect measures of cell mass must be used to characterize the performance of the bioreactor. Due to the same reasons, removal of a cell associated product can also be problematic with these reactor configurations.

Microcarrier technology provides a large amount of surface area for cell growth on small, spherical beads (90 to 250 microns in diameter) which are suspended in a stirred tank bioreactor. High surface to volume ratios can be achieved resulting in a highly efficient production system on a bioreactor volume basis. The technology provides a homogeneous cell culture environment with the capability to quantify cell mass and harvest cell associated product during the cultivation. Since the bioreactor is a stirred tank, well established cleaning and sterilization procedures, as well as overall tank design is readily available from the fermentation industry for commercial applications. The commercial manufacture of Polio Vaccine using microcarriers at the 1000–1500 liter scale illustrates the scale-up potential of this approach. The commercial production of a Rabies vaccine and a Foot and Mouth Disease Vaccine using microcarrier culture further illustrates the proven scale-up potential of this method.

Although many cell lines and viruses have been propagated on microcarriers, many challenges remain in implementation of this technology at commercial scale. Attaining a low shear environment throughout the cultivation and maintaining a viable culture for sustained product formation through extended cultivation periods can be difficult. Selection of the proper microcarrier and culture conditions is often critical in producing the desired product. The propagation of Hepatitis A is a good example of these challenges. Junker, B. et al., ("Evaluation of a Microcarrier Process for Large Scale Cultivation of Attentuated Hepatitis A," Cytotechnology, Vol. 9, 1–3, 1992) described the evaluation of CYTODEX 3 collagen-coated Sephadex Microcarriers microcarriers as the substratum of MRC-5 cells growth and subsequent infection by hepatitis A virus. A major contributor to the low hepatitis A titers from the microcarrier cultures was attributed to the fact that the cells gradually fell off the beads during the infection period. Based on these results, microcarrier technology was reported to be suboptimal for commercial scale production of hepatitis A virus. Because culture of hepatitis A virus in exemplified in the instant patent disclosure, a brief review of the methods used to culture this virus is in order.

In 1973, Feinstone et al., [Science 182, p 1026] identified the etiologic agent of infectious hepatitis, later known as hepatitis A virus, (HAV), using immune electron microscopy. In vitro culture of hepatitis A virus (HAV) was reported by Provost et al [P.S.E.B.M 160, p 213, 1979] according to a process whereby liver from HAV infected marmosets was used as an inoculurn for liver explant culture and fetal rhesus kidney (FRhK6) cell culture [U.S. Pat. No. 4,164,566]. In a later invention, direct inoculation of a HAV, which had not been previously passaged through a subhuman primate, was successfully used to initiate in vitro propagation of HAV [Provost et al., P.S.E.B.M. 167, p 201 (1981); U.S. Pat. No. 5,021,349].

From this work, attenuation of HAV through in vitro culture was demonstrated. In addition, it was demonstrated that upon repeated passage in vitro, HAV cultures became more productive and replication rate accelerated as the virus became adapted to the cultured cells. A further development was the demonstration of protective efficacy of both the live attenuated virus [Provost; et. al., J. Med. Viol. 20, p 165 (1986)] and the formalin inactivated HAV [U.S. Pat. No. 4,164,566; U.S. Pat. No. 5,021,348; Provost et. al., in *Viral Hepatitis and Liver Disease,* p 83–86, 1988—Alan R. Liss, Inc.]. From the foregoing work, it has become clear that either an inactivated or attenuated, immunogenic HAV are possible vaccine candidates. However, a reproducible, commercial scale process for production of high purity antigen is needed if a safe HAV vaccine is to be commercially available for use in humans.

Various methods have been described to culture HAV for vaccine production. Thus, Provost et al. (U.S. Pat. No. 5,021,348) described a process whereby, in a preferred method, a cell culture of MRC-5 cells was infected with HAV. According to that disclosure, the virus and cells are grown according to conventional methods in monolayer. In U.S. Pat. No. 4,783,407, HAV was grown in Vero cells (a type of primate kidney cell). In U.S. Pat. No. 4,301,209, high titer HAV production in a hollow fiber capillary unit was described. In U.S. Pat. No. 4,412,002 a process whereby HAV was isolated from persistently infected cells was described. In EP 0 302 692, HAV culture in roller bottles was described. In all of these systems, the large scale production of HAV required for a commercial process was not feasible or was severely limited by the amount of surface area available for cell sheets to be established for HAV infection.

In 1984, Widel, et al., published on the propagation of wild type Hepatitis A in a fetal rhesus monkey kidney (Frh-k) cell line grown on CTYODEX 3 microcarriers at 37° C. (Widell, A. etal., "A Microcarrier Cell Culture System for Large Scale Production of Hepatitis A Virus." J. of Virological Methods, Vol 8, 63–71, 1984). There was no mention of cell attrition or microcarrier aggregation using CTYODEX 3 microcarriers as the growth surface for Frh-k cells. Since the same microcarrier system was determined by Junker et al., to be unsuitable for the production of attenuated virus in MRC-5, these culture systems are clearly very different. Therefore, the MRC-5 human diploid cell line, which is preferable over the Frh-k cell line derived from monkeys for the production of a human vaccine, can not be successfully cultivated to produce Hepatitis A vaccine using the process described by Widel due to the tendency of MRC-5 cells to form microcarrier aggregates. Since the methodology described by Widel is limited to FRH-k cells where aggregation and cell attrition were not addressed, no knowledge of how to overcome these problems encountered when using MRC-5 cells could be gained from this work.

Aggregation of cells in microcarrier cell culture is quite common and has been mentioned in the published literature since the mid 1970s. However, few papers have specifically addressed this topic. A few relevant publications are discussed below:

Varani, et al., (1983) compared the growth of MRC-5 diploid cells and two transformed cell lines on glass coated microcarriers and charged DEAE-dextran microcarriers (Varani, J., etal., "Growth of Three Established Cell Lines on Glass Microcarriers." Biotech. and Bioeng., Vol. 25, 1359–1372, 1983). Microcarrier aggregation occurred with all three cell lines on the glass coated microcarriers while only one continuous cell lines on the glass coated microcarriers while only one continuous cell line aggregated with the dextran microcarrier. Scanning electron microscopic (SEM) analysis illustrated a dramatic difference in the way the cells attach to the two surfaces. In the glass microcarrier cultures, the cells attach by long filopodia while for the DEAE dextran microcarriers the attachment occurs across the entire cell edge. This difference in attachment mechanism may be an important factor in the stability we report of the MRC-5/SOLOHILL glass coated system over MRC-5/dextran systems.

Goetghbeur and Hu (1991) demonstrated that cell aggregates could be induced to form with a number of cell lines in the presence of small charged microspheres with a diameter of about 20 microns (microcarriers are typically 90–250 microns; Goetghebeur, S. and W. S. Hu, "Cultivation of Anchorage-Dependent Animal Cells in Microsphere-Induced Aggregate Culture." Appl. Microbial. Biotech., Vol 34, 735–741, 1991). Two transformed cell lines grown in this way were found not to spread, but rather exist as rounded up multilayered populations. A diploid cell line was also grown on these spheres as aggregates, but the cell shape was irregular, see U.S. Pat. No. 5,114,855. Since the spheres used in Hu's work are much smaller than conventional microcarriers, the aggregate formation described in the instant patent disclosure does not fall in the domain covered by Hu's patent. It is unlikely that a reduction in size to the range in Hu's patent would be applicable for the manufacture of Hepatitis A.

Borys and Papoutsakis (1992) investigated ways to inhibit cell aggregate formation with Chinese hamster Ovary K1 cells grown on CYTODEX 3 microcarriers (Borys, M. C., and E. T. Papoutsakis. "Formation of Bridges and Large Cellular Clumps in CHO-cell Microcarrier Cultures: Effects of Agitation, Dimethyl Sulfoxide, and Calf Serum," Cytotechnology, Vol 8, 237–248, 1992). The emphasis of this work was on overgrowth of transformed cell lines during microcarrier culture and did not address the growth of diploid cell lines as aggregates on microcarriers. Increased agitation was found to reduce aggregation and increase cell death due to the breaking of cellular bridges between microcarriers. Our studies, disclosed herein, with MRC-5 and glass coated microcarriers are in agreement with these results. We have found that agitation did reduce the rate of aggregation of MRC-5 cells in the glass coated microcarrier system with an increase in cell death. We also found aggregation to be an irreversible phenomenon under culture conditions.

A significant amount of work has been done to induce continuous cell lines to grow as cell aggregates in suspension culture. Tolbert, et al., (1980) published an early account of this approach and cited a patent on the "adaptation of cell lines to suspension culture" (Tolbert, W. R. etal., "Cell Aggregate Suspension Culture for Large-Scale Production of Biomolecules," In Vitro, Vol 16(6), 480–490, 1980). Since MRC-5 cells are human diploid, they require cell spreading for biological activity and are therefore not amenable to this approach.

Thus, while reports exists disclosing that MRC-5 cells can be grown on glass microcarriers as cell-microcarrier aggregates and that Hepatitis A can be produced from a CYTODEX 3 microcarrier culture, as noted above, the instability of the MRC-5 cell/CYTODEX 3 microcarrier system has led those skilled in the art to believe that microcarrier culture is not adaptable to efficient HAV production. Disclosed herein is a uniquely stable microcarrier aggregate system which overcomes previous problems in producing Hepatitis A from MRC-5 cells on microcarriers. This disclosure also identifies methodology developed to integrate the microcarrier process into an existing downstream HAV purification system.

SUMMARY OF THE INVENTION

This invention provides a process to create a culture of microcarrier aggregates which retain cell populations throughout an extended infection phase for the manufacture of a viral vaccines. Hepatitis A production in MRC-5 cells has been shown to be problematic due to the sloughing of cells from the microcarrier during the infection period. The use of the glass coated microcarrier system and methodology described herein overcomes this problem through the creation of a stable microcarrier aggregate capable of retaining the cells in viable state for maximum virus production in microcarrier culture. The method is applicable to production of other viruses where virus productivity can be enhanced by creating a stable culture during an extended infection period. Our experiences with CYTODEX 3, a collagen coated microcarrier, agree with earlier reports showing that in that system, the formation of aggregates was erratic and the cell population was unstable upon entering the stationary phase. In sharp contrast to the foregoing, we have discovered a glass-coated microcarrier based process which supports extended, stable culture of cells. We have also developed a method to break-up the microcarrier aggregates and lyse the cells with a detergent buffer system. Nuclei remain intact during this procedure so they can be filtered out before entering the purification process. The lysis is then amenable to downstream processing according to established virus purification processes. Vaccine applications for this process include production of any virus which an be propagated in an aggregated microcarrier culture and recovered from the bioreactor. Anchorage dependent cells which can form aggregated cultures include MRC-5, WI38, Vero, and Chick Embroy Fibroblasts. Viruses which could be propagated in these hosts cells include, but are not limited to Hepatitis A, Varicella, Measles, Mumps, Rubella, Poliovirus, Herpes virus and Rotavirus.

The process provides a method to utilize the proven commercial scale-up advantages of microcarrier technology for cell growth in the production of viral vaccines, such as hepatitis A, which require extended culture times. The successful application of microcarrier technology for the production of Hepatitis A or other products where cultivations extend into the stationary phase, is shown here to be due to the proper selection of a microcarrier/cell system which produces aggregates which provide the microenvironment for extended cell viability and product formation. The formation of aggregates, as described herein, protects the cells from the shear generated by suspending the microcarriers. The aggregates possess approximately 50–60% void space which provides convective transport of nutrients through out the aggregate and lowers the density of the aggregate for easier suspension of the particles. Aggregate formation also provides close cell to cell contact, increasing cell to cell spread of viral infections, and provides tissue-like contacts for product formation.

DETAILED DESCRIPTION OF THE INVENTION

This invention is a process for the replication and growth of viruses in microcarrier cell culture. Vaccine applications for this process include production of any virus which can be propagated in an aggregated microcarrier culture and recovered from the bioreactor. Anchorage dependent cells which can form aggregated cultures include, but are not limited to, MRC-5, WI38, Vero, and Chick Embryo Fibroblasts. Viruses which could be propagated in these hosts cells include, but are not limited to Hepatitis A, Varicella, Measles, Mumps, Rubella, Poliovirus, Herpes virus and Rotavirus. According to this process, cells are grown to an optimal density on glass-coated microcarriers and are infected with virus. According to one embodiment of this method, cultures are perfused with media through the cell-growth and virus-infection stages. At the end of the infection, the microcarriers are harvested. The product virus is collected from either supernatant medium or lysed cells. In the case of cell associated viruses which are not released into the media or viruses which require additional steps to be released in sufficient yield (such as freeze/thaws or fluid shear), the harvest method described in this invention for release of virus from aggregated microcarrier cultures can be employed. The harvest can involve fluid shear or fluid shear coupled with a detergent to permeabilize the cells.

Perfused MRC-5 cells cultured on glass-coated microcarriers and infected with hepatitis A virus exemplifies the process of this invention. An important element in the production of viruses in perfused microcarrier culture is the stability of the cell population over the course of the infection process. This observation is particularly significant for slow-growing viruses such as hepatitis A virus (HAV). In the production of HAV, the preferred cells are MRC-5, although similar cells, such as WI38 or VERO, which are acceptable for human vaccine production, may be used. In the case of HAV and MRC-5 culture, the cell population must remain stable over the course of a 21 day infection process. During this time period, the cells are in stationary phase.

Figure 19:
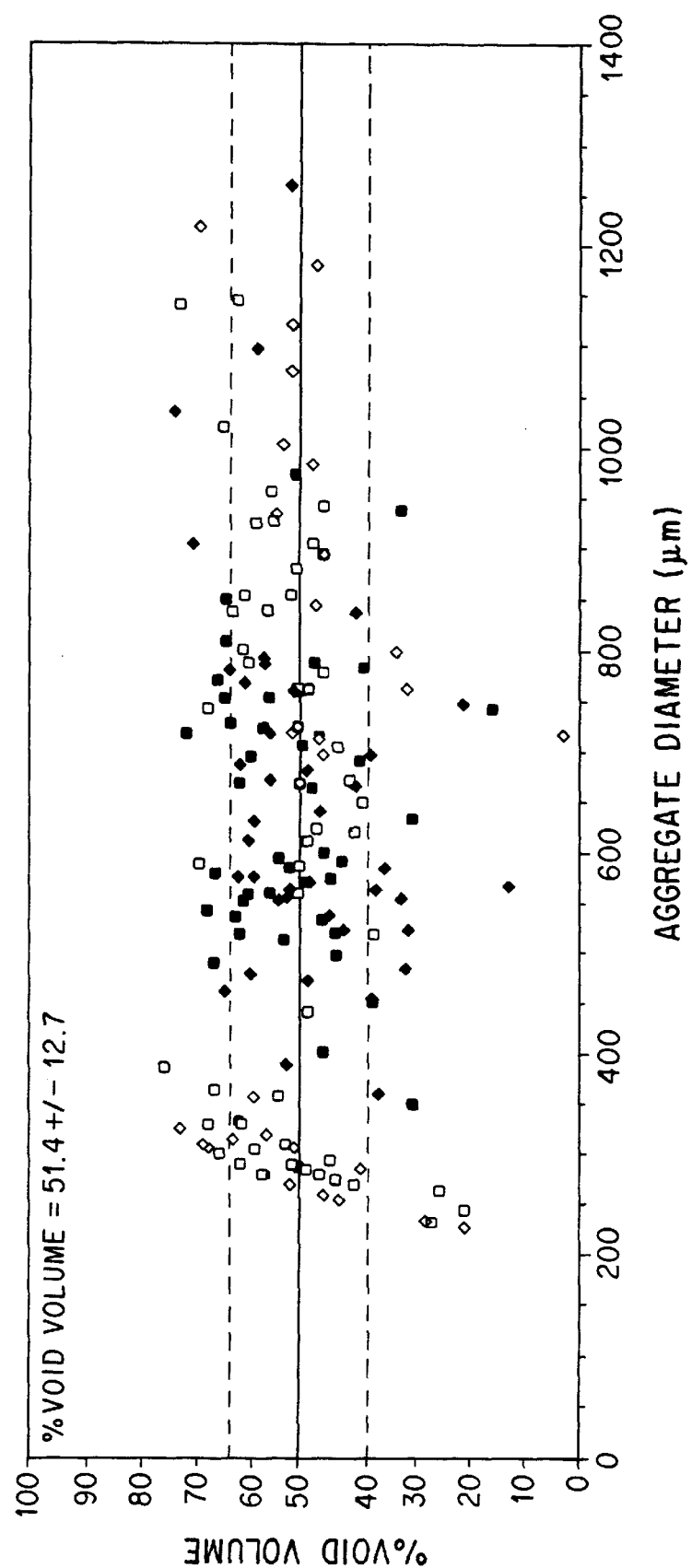
FIG. 19. % void space within a MRC-5/glass coated microcarrier bead is approximately 50% irrespective of aggregate diameter.

In microcarrier screening studies involving microcarriers from various manufactured including Pharmacia (CYTODEX 1, 2, & 3glass and collagen coated microcarriers), SOLOHILL Laboratories Mat Tek (Plastek), and Mitsubishi Kasei (Discarrier), we discovered that only SOLOHILL Glass Coated Polystyrene beads establish a stable culture through the stationary phase. In this system, MRC-5 cells grow in microcarrier aggregates which increase in size as the culture progresses. In the screening of various microcarrier systems for commercial applications it is common to screen out microcarrier types which cause significant aggregation with the cell line used. Increases in agitation, reduction in calcium concentration, and reduction in serum concentration are common methods employed to minimize or eliminate aggregation. In the MRC-5 system, we have discovered that through proper cultivation techniques, the glass coated microcarrier system forms an aggregate structure with MRC-5 cells which is an ideal environment for the propagation of viruses for vaccine production. The aggregate is formed through cellular bridges via cell to cell contact. As the number of microcarriers grow, the cells grow in the void space providing a tissue like growth morphology. The void space is known to be 50 or 60% of the aggregate volume as illustrated in FIG. 19, while the cell mass occupies only 1–2% of this space. Therefore, unlike bioreactor systems or immobilization methods which result in diffusional limitations through the cell mass, the cells are distributed through the aggregate with sufficient void space for convective transport of nutrients and product through the bead. The aggregate is resistant to pH changes beyond that seen in cell cultivations and EDTA at concentrations up to 1 mM indicating that receptor bonds which were likely involved in the initial formation of the aggregate are not required to maintain the aggregate structure. Since the aggregates can be completely disassociated by trypsinization, the aggregate structure is most likely maintained by extracellular matrix proteins secreted by the cells. Other MRC-5 cell/microcarrier systems form aggregate which are not stable like the one created with the glass coated microcarrier system we describe herein. Therefore, according to our teaching, selection of glass coated microcarriers for cultivation of cells results in the creation of a stable aggregate structure for the propagation of viruses for vaccine manufacture.

Figure 16:
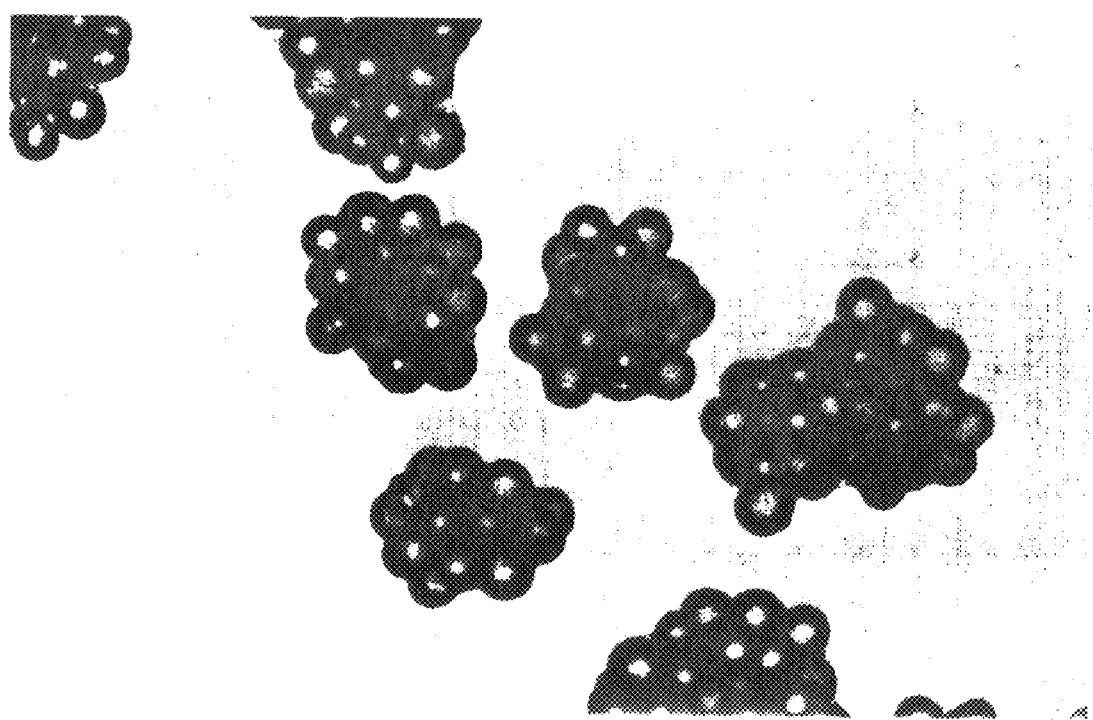
FIG. 16. Microcarrier Aggregate after 5 days in culture produced by the methodology of this invention using MRC-5 cells and Solohill Glass Coated Microcarriers. The aggregate sizes are similar and no single microcarriers without cells are present.
Figure 17:
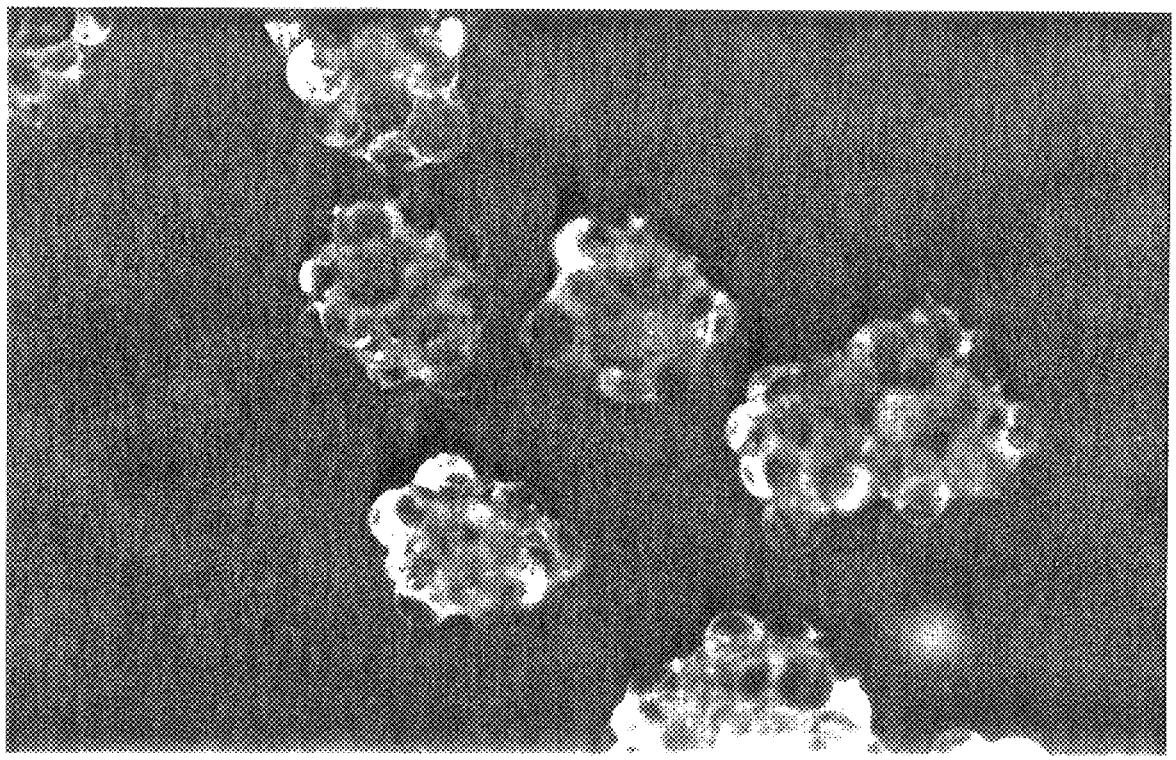
FIG. 17. MRC-5/Solohill Glass Microcarrier Aggregates stained with Flourecein Diacetate. Green flourescence indicates viable cells.
Figure 18:
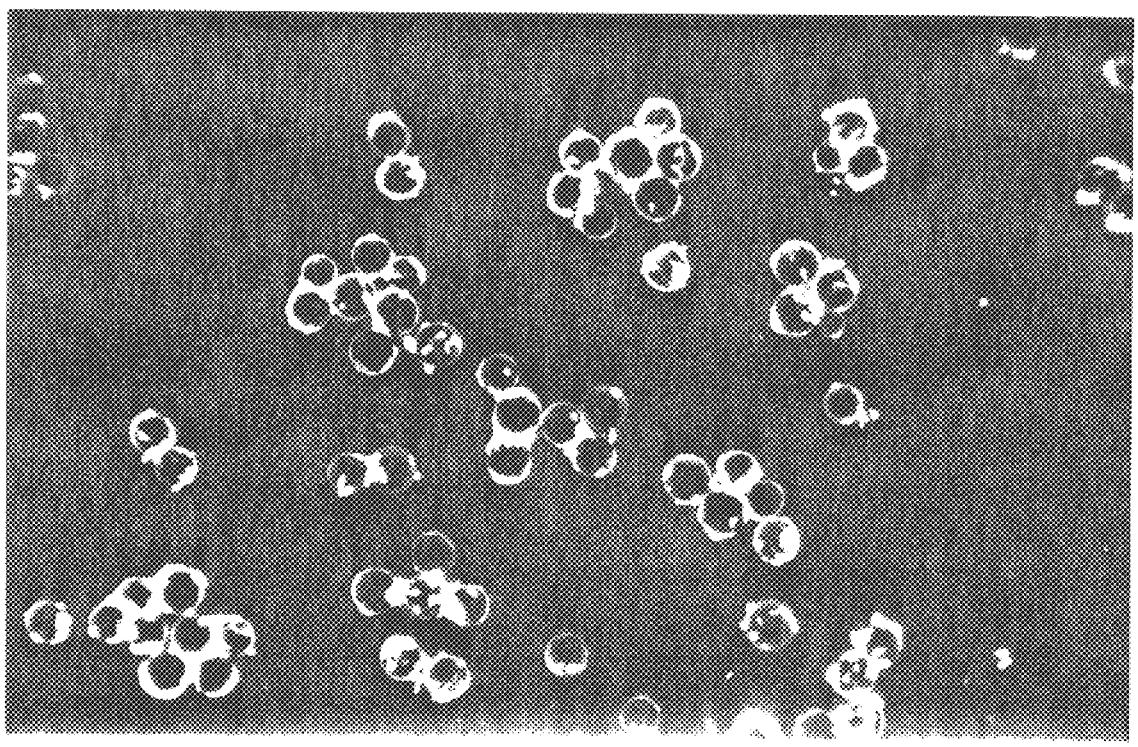
FIG. 18. Initial Aggregation of the MRC-5/Solohill Glass Microcarrier System on Day 1 of the Cultivation. Flourescien diacitate was used; viable cells flouresence green.
Figure 20:
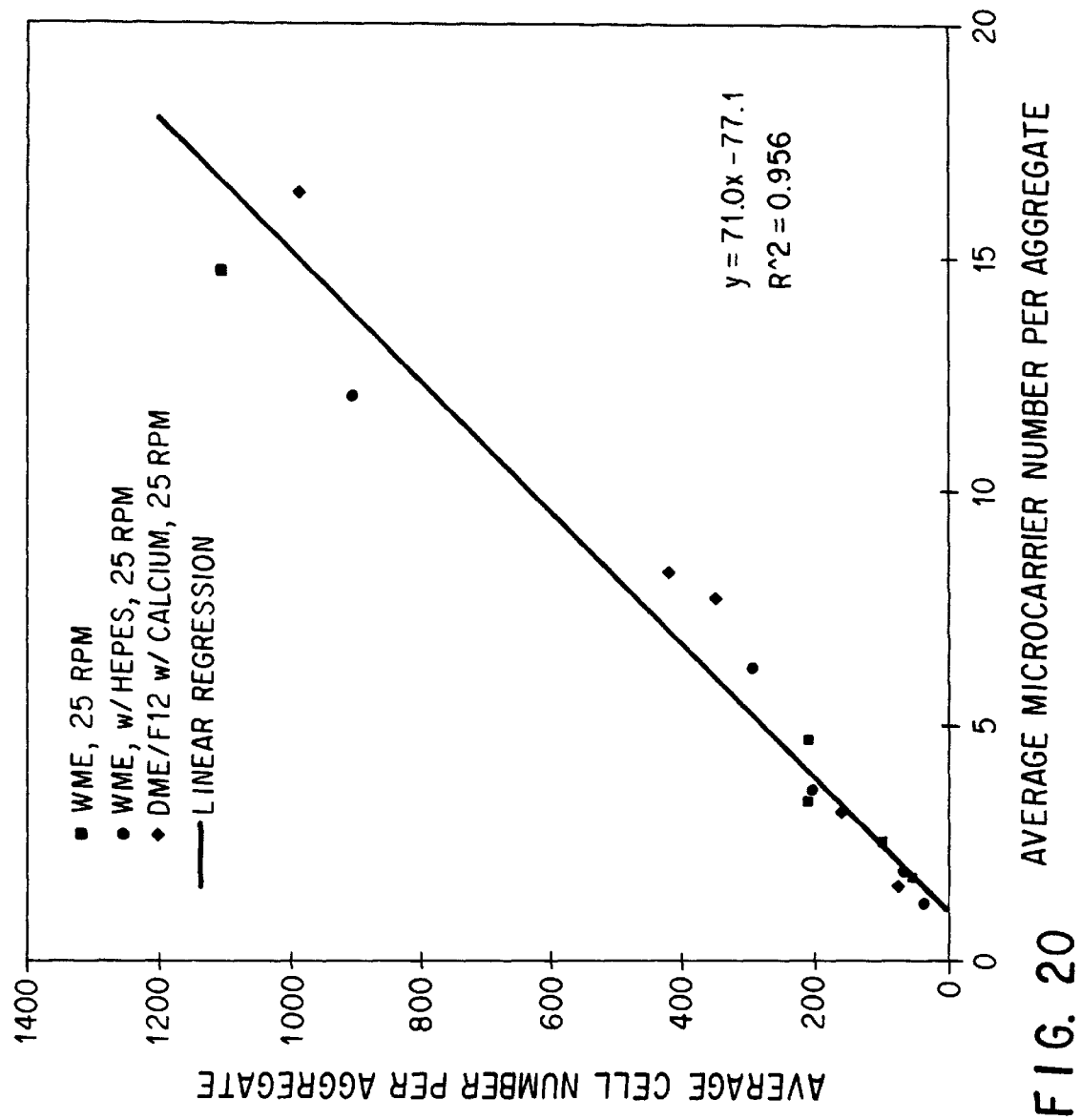
FIG. 20. Aggregate Formation during Cell Growth. The aggregate size increases proportionally to the increase in number of cells per aggregate.

Once we selected the glass-coated microcarrier for cell growth based on stability during the infection phase, the proper cultivation conditions must be employed for uniform aggregate formation. FIGS. 16–18 illustrate aggregate formation through the methodology described in this invention. Uniform, predictable aggregate formation is important for consideration of such a system for commercial production of a viral vaccine. First, the cell attachment must be uniform across the microcarrier population since aggregation occurs by cell to cell interactions, not cell to microcarrier interactions. This is known from the fact that beads with no cells attached will remain as such throughout a cultivation while aggregation occurs with the microcarriers with attached cells. Under proper attachment conditions, all the microcarriers have cells attached and thus all join to form aggregates in culture as illustrated in FIG. 20. This is achieved by inoculating at more than 5 cells per bead which is established practice in microcarrier work. Typsinization procedures, agitation, pH, temperature and serum concentration also play a roles in uniform attachment. The growth of aggregate size as a function of cell growth within the aggregate is illustrated in FIG. 20. The hydrodynamic environment established by the agitation employed is important to the growth of the aggregates in culture. The RPM should be maintained at or just above the critical off bottom suspension stirring rate which corresponds to the stirrer speed when no microcarrier remains stationary on the bottom for more than one second. The impellers should be about half the tank diameter or greater to minimize the RPM required while maximizing bulk mixing. Smaller impellers create high shear zones near the impeller which can break cellular bridges, thus reducing aggregation and cell viability. Unhealthy cultures will increase in aggregate size. This is expected to be due to DNA released during cell lysis acting as the mediator for increased aggregation. Employing a feeding strategy (medium replishment) which maintains cell viability minimizes further aggregation in the stationary phase.

The critical off bottom suspension for the aggregates is lower than that of single microcarriers which would not be expected due to the larger size of the aggregate. The reason is due to the decreased density of the aggregate since the void volume (filled with media) is 50–60% of the aggregate volume and probably due to the hydrodynamics of suspending the aggregate through dissipation of energy on the heterogeneous surface. The aggregates do, however, settle much faster than single microcarriers. These properties are advantageous for processing at manufacturing scale. Thus, we have discovered that the cellular aggregates, rather than being undesirable, as had been previously though, provide a stable environment for the stationary phase cells and for viral infection and growth.

SOLOHILL Glass Microcarriers consist of a polystyrene bead of predetermined size and density, coated with a thin layer of glass according to a patented production process licensed to SOLOHILL Labs, Inc. (U.S. Pat. Nos. 4,029,045, 4,448,884, and 44,564,532). Since the density of glass is 2.4 g/ml, it is necessary to coat a low-density microcarrier to provide a glass surface of low density (density of 1.02 to 1.04 g/ml). A microcarrier density just above the density of the fluid medium is critical to minimize shear damage to the cells while suspending the microcarriers in a stirred tank. Thus, any glass coated microcarrier displaying this property is usable in the instant process, and the SOLOHILL glass microcarriers in a stirred tank. Thus, any glass-coated microcarrier displaying this property is usable in the instant process, and the SOLOHILL glass microcarriers are but one, commercially available example. SOLOHILL glass microcarriers have been utilized to grow a number of anchorage dependent cell lines including Vero (monkey kidney), CEF (chick embryo fibroblasts), BHK (hamster kidney), MRC-5 (Human embryonic lung diploid fibroblast), HFF (human foreskin fibroblasts), and MDBK (Mardin-Darby bovine kidney). By adhering to the method disclosed herein, all of these cell-types may now be used in extended, aggregated cell-culture to produce viruses which can infect and grow these cells. The glass substratum has been reported to result in a different attachment morphology than that seen on CYTODEX microcarriers from Pharmacia LKB Biotechnology (Varani, J., etal., Substrate-dependent differences in growth and biological properties of fibroblasts and epithial cells grown in microcarrier culture, J. Biol. Stand. Vol 13, pp 67–76, 1985). These differences combined with proper cultivation conditions disclosed herein were used to induce stable aggregate formation for the production of a viral vaccine.

In one embodiment of this invention, hepatitis A virus (HAV) variant passage 28 (P28) of stain CR326F was used to infect MRC-5 cells grown on microcarriers, for merely illustrative purposes, and the production material was cultured at passage 29 (P29). P28CR326F is an attenuated HAV strain. Other strains and/or serotypes of HAV are encompassed by this invention, including HAV strains that can be attenuated by conventional techniques known in the art. Other suitable cell lines for HAV propagation include Vero, Fla., WI-38 and FRhK6 cells. These and other systems for HAV propagation in cell cultures are discussed in Gerety, R. J. "Active Immunization Against Hepatitis A," in Gerety, R. J. (ed.) *Hepatitis A* Academic Press 1984, pp. 263–276; and Ticehurst, J. R., Seminars in Liver Disease 6, 46–55 (1986). In principle, any cell line such as any human diploid fibroblast cell line, can serve as a host cell for HAV provided that it is susceptible to HAV infection. The preferred cell line is MRC-5. It be understood by those of skill in the art that the scope of the present invention encompasses, in addition to the passage 18, P18 or p28, of strain CR326F of HAV, and other HAV variant or strain, whether attenuated or virulent as well as other viruses which can be cultured on anchorage dependent cells. Attentuated variants or strains may be isolated by serial passage in cells, animals, or by other methods. See, for example, Provost, P. J. et al. Proc. Soc. Exp. Biol. Med. 170,8 (1982); Provost, P. J. et al. J. Med. Virol. 20, 165 (1986); U.S. Pat. No. 4,164,566 and 5,021, 348 for details on attenuation. The culture method of the present invention is readily and easily adaptable to attenuated or virulent HAV strains.

In a preferred embodiment of this invention, MRC-5 cells are infected at a multiplicity of infection (MOI) of HAV sufficient to achieve efficient cell culture infection. An MOI of about 0.05–1 is acceptable. Stock seed is conveniently generated by using HAV from the supernatant fraction of a stationary culture infected with HAV and incubated for about 28 days. The HAV is allowed to replicate in the stationary culture to a peak of virus production. Other methods such as microcarrier culture or the COSTAR CUBE could be used for stock seed generation. The cell culture medium may be any medium which supports active growth of MRC-5 cells and HAV replication.

The process of this invention is better understood with regard to the following steps or phases:

Step 1: Microcarrier Preparation

A suitable bioreactor for stirred suspension culture of mammalian cells is charged with dry, glass-coated microcarrier beads. The beads are suspended in WFI Quality Water and sterilized in situ. Following sterilization, the water is drained and a suitable sterile medium for culturing the cells of choice for the particular virus to be grow is added to the bioreactor. To ensure complete replacement of water and equilibrium of the beads, the medium is preferably replaced up to three times. For HAV culture, we have found the use of Williams Media E (serum free) is acceptable at this stage. A target of about 20 grams/L to 75 grams/L of microcarriers to media, and preferably about 40 grams/L to 60 grams/L is desirable.

Step 2: Cell Inoculation

Once the microcarriers have been equilibrated in the medium and temperature (30°–37° C.) of choice, cells, preferably in late log phase, are seeded into the culture vessel. For small scale work, NUNC CELL FACTORIES (NCFs), which are small multilamellar cell culture units within which cells may be grown in monolayer according to the manufacturer's directions, are convenient for this purpose. The inoculum cell concentration is 5–10 cells per microcarrier bead which corresponds to about 100,000 ($1\times10^5$) cells/mL at the bead loadings used. For a small microcarrier culture of about 600 mL, about $6\times10^7$ cells are required. From one confluent ten-layer NCF, approximately $5\times10^8$ cells may be harvested using trypsin. These ratios are easily scaled upward for larger microcarrier culture inocula by using additional NCF or, if necessary, a seed microcarrier culture. Once the cells have been trypsin harvested and neutralized with serum containing media, they are pelleted by low-speed centrifugation and resuspended in medium containing about a 10% iron supplemented calf serum, or they are simply diluted with media containing about 10% iron supplemented calf serum. By using one part of cell inoculum to nine parts of microcarrier/serum free culture medium, a 1% iron supplemented calf serum final concentration is attained. This ratio may naturally be modified by modifying the concentration of serum added to the resuspended cell inoculum or by modifying the inoculum to bioreactor volume ratios. A 1% serum concentration at pH 7.6–7.9 was found to provide uniform cell attachment.

Once inoculated, the cells are allowed to attach to the microcarriers for about three hours (although longer or shorter times are acceptable and the precise amount of time provided for attachment is not critical) using a rate of agitation sufficient to achieve the critical off-bottom suspension, which is the minimal rate of agitation (revolutions per minute, rpm, of the impeller) necessary to achieve a condition in which no microcarriers spend any more than about 1 second at the bottom of the stirred bioreactor. This is achieved by inspection and appropriate modification of the impeller speed, and is a simple procedure with which those of skill in the art are acquainted.

Step 3: Perfusion Culture of Cells to Late Log Phase

Once the cells have been given sufficient time to attach to the microcarriers, the medium is supplemented with additional serum for cell growth. For MRC-5 cell culture for HAV production, addition of sufficient iron supplemented calf serum to achieve a 10% serum concentration is preferred. Serum concentration may vary with other media formuations as those skilled in the art will appreciate.

After about 24 hours from cell attachment and equilibrium with any adjusted serum conditions, a perfusion inlet/outlet system is established whereby medium is removed and replenished at a rate of about 0.7 to about 2, and preferably about 1.3, volumes of medium per day. Monitoring of glucose, lactate and ammonia provides a method for ensuring that nutrient depletion and pH fluctuations do not occur. Those of skill in the art are well acquainted with the techniques of monitoring these parameters and of methods for achieving their stability. For example, if the glucose supply is found to be limiting, the perfusion rate may be increased. If the pH is found to be too acidic due to lactate production and accumulation, addition of mild alkali or increase in the perfusion rate would control this undesirable trend. Sterile filtered air is provided in the headspace of the bioreactor, and at small scale, a surface impellor may be used to advantage to increase gas transfer by disrupting surface tension at the air-liquid interface.

Once the perfusion has been established, the cells are allowed to grow to late exponential (log), or early stationary phase. Typically, with MRC-5 cells in Williams Media E supplemented with 10% iron supplemented calf serum, this requires a period of about six days. While the length of time provided for cell growth is not critical, it is desirable that sufficient time be provided so that good cell growth and aggregation has been achieved.

Step 4: Infection

Typically, a stock seed of infectious virus is conveniently stored frozen. However developed, a stock of infectious virus is used to infect the cells at a multiplicity of infection (MOI) of about 0.05 to about 1, and preferably about 0.1 The perfusion is stopped during this infection period to allow attachment of virus to cells for about two hours. Once sufficient time has been provided to achieve efficient attachment of virus to cells, the perfusion is restarted. Samples may be taken from the culture every week, and after a sufficient amount of time, depending on the virus, the complete bioreactor is harvested. For HAV grown on MRC-5 cells in the system we have described, peak HAV production is typically achieved by about 14–28 days after infection.

Step 5: Viral Harvest

As a first step in viral harvest, the agitation is stopped and the virus infected cells attached to microcarriers are allowed to settle by gravity. At the manufacturing scale, methods to wash the aggregates, such as the use of a filtration device, are preferable. The culture supernatant is removed. For HAV, the bulk of virus is found within the cells and must be liberated by cell lysis. This is achieved by breaking up the cellular aggregates in a harvest solution. Preferably, the harvest solution contains a component effective to render the cells permeable to HAV. Such components are known in the art. Preferably, a detergent such as Triton X-100, NP-40, or an equivalent is supplied at the lowest effective concentration possible, to facilitate later removal. One detergent that has been found acceptable for this purpose is TRITON-X100, which may be provided at a concentration of about 0.1% in a suitable buffer such as 10 mM Tris-CHl, 0.1 mM $MgCl_2$.

An efficient method for breaking aggregates in our system comprises passing the microcarriers through the recycle loop into which is includes a series of orifices of decreasing diameter. Diameters of 1/16", then 3/64", then 1/32" are used and the contents of the bioreactor are recycled at about 500–1000 mL/minute, until all the aggregates (by microscopic inspection of samples) have been disrupted. Upon scale-up of this step, the fluid shear required to break up the aggregates is achieved by properly sizing the orifice diameters for the increased flow rate during the harvest to achieve the same linear velocity. As linear velocity=flow rate/area of the orifice, conditions for aggregate disruption may be achieved by obtaining linear velocities in the range 1010 m/minute–2020 m/minute, regardless of the scale. The lowest diameter (1/32", about 0.8 mm) is approximately Five times the diameter of a single microcarrier (about 150 $\mu$m). At larger scales of production, a larger orifice is used to avoid fouling, but to compensate, the flow-rate is simply increased to provide linear velocities in the range described above. This is a sufficiently narrow diameter to achieve efficient aggregate break-up but also sufficiently large that fouling, particularly after passage through the larger orifices, is minimized. Other techniques, including but not limited to sonication, could also be used. The resulting slurry of microcarriers is allowed to settle and the cellular debris containing the virus is decanted and stored. The bioreactor is charged with additional detergent containing buffer and the contents of the bioreactor are recycled through the external loop and orifices again to retrieve trapped virus. Once again the slurry is allowed to settle and the supernatant is combined with the stored supernatant. At this stage, a hemacytometer count of nuclei found in the supernatant provides a good estimate of the number of cells harvested. The supernatant is filtered, preferably through a 5 $\mu$m filter to remove the nuclei and the supernatant is then subjected to downstream processing as desired. A process amenable to HAV purification is provided below.

Step 6: Purification of HAV

The HAV produced in culture according to the instant invention may be purified according to methods known in the art or it may be directly used as a vaccine if attenuated. It may also be inactivated according to methods known in the art, primary among which is formalin inactivation. For details on these steps known in the art, see for example U.S. Pat. No. 4,164,566; 5,021,348; EP 0 302 692; and U.S. Ser. No. 07/926,873, filed on Aug. 10, 1992, now abandoned.

Step 7: Vaccine Inactivation and Formulation

Additional processing steps of conventional and well known character are or may be needed to prepare purified HAV capsids for vaccine use. For example, treatment with formalin, sterile filtration and adsorption to carriers or adjuvants are the typical basic steps for preparing a formalin-inactivated vaccine. See, for example, Provost, P. J. et al. Proc. Soc. Exp. Biol. Med. 160, 213 (1979); Provost, P. J. et al. J. Med Virol. 19,23 (1986). HAV can be inactivated by heat, pH changes, irradiation, treatment with organic solvents such as formalin or paraformaldehyde. Typically, HAV inactivation is carried out at a 1/4000 ratio of formalin. The inactivated HAV is then adsorbed or coprecipitated with aluminum hydroxide to provide adjuvant and carrier effects. Efficacy of an inactivated HAV vaccine has been shown [New England J. of Med. 327: 453–457, (1992)]

For the purposes of comparison of the instant process with a monolayer cell culture-virus production process, MRC-5 cells were planted into 2 large-scale COSTAR CUBE bioreactors and 3 microcarrier cultures. The perfusion rate for the microcarrier cultures were 0.7 and 1.5 bioreactor volumes/day which encompass the 1.3 bioreactor volumes per day used in the COSTAR CUBE. The microcarrier loading was chosen to obtain a similar cell density as the production COSTAR CUBE bioreactors so direct comparisons could be made between the two bioreactors. The microcarrier cultures were stable throughout the infection period and had similar metabolic rates as the COSTAR CUBE bioreactor with regard to glucose and lactate. Microcarrier lysate and one liter of COSTAR CUBE lysate purified with similar efficiency and handling ease using a downstream process adapted to HAV purification. The Hepatitis A production was about half of the COSTAR CUBE process on a per cell basis indicating the need for optimization of the infection process in microcarrier culture. The volumetric productivity per liter bioreactor volume was also about half that of the COSTAR CUBE; however with this method, there is potential to more than double the cell density, and thus volumetric productivity, though increased microcarrier loadings. The MRC-5 cell population was maintained in stable microcarrier aggregates with no loss of cells during the 21 day infection process. All other microcarrier types tested resulted in attrition of the MRC-5 population from the microcarriers after the growth phase and were thus unsuitable for virus production. We have achieved final cell density in the microcarrier cultures of 2.2–2.4×10$^6$ cells/ml which is similar to the estimated 2.6×10$^6$ cell/ml density produced in the COSTAR CUBES.

The glucose consumption rate and lactate production rate in perfused microcarrier culture were quite similar to that which occurred in perfused COSTAR CUBES. A stoichiometric conversion of glucose to lactate was seen in both systems. The ammonia production, a by-product of principally glutamine metabolism was about half in the microcarrier system where a 2 mM glutamine feed was used instead of 4 mM glutamine feed in the COSTAR CUBES. At 21 days post infection the microcarrier culture produced an average of 112 units per million cells and 258 units per liter bioreactor volume. These yields are 40–50% and 38% of those achieved in COSTAR CUBES, respectively. The virus growth curve indicated over 50% of the virus was already produced by day 14 with a substantial decrease in virus growth rate over day 14 to day 21. It is not clear whether the decreased cellular yield is due to not all the cells participating in the infection, less productivity per infected cell, or leakage of virus into the media before harvest. The aggregates were stable through 2 saline washes and even upon addition of the 0.1% Triton. The aggregates were broken up by controlled fluid shear through a series of orifices which were installed in a recycle loop with the bioreactor. Nuclei were released (and thus easily quantified) and removed by filtration through a 5 μm Durapore filter allowing the lysate to be processed according to an established purification process. SDS PAGE of solvent extracted material showed the 3 characteristic bands for Hepatitis A and a fourth band at 66,000 molecular weight which probably corresponds to serum derived BSA which was not completely removed during the harvest saline washes.

One of the most significant aspects of this invention is that we have demonstrated that MRC-5 cells can be maintained on microcarriers in a stable state throughout the 3 week Hepatitis A infection for the production and quantitative purification of Hepatitis A. The stability of the system is attributed to the unique properties of he aggregates formed during the growth of MRC-5 cells on glass coated polystyrene microcarriers.

The data presented here provides a comparison of a perfused microcarrier process and a monolayer cell culture manufacturing process at similar cell densities and perfusion rates. Metabolic indicators such as glucose utilization, lactate accumulation, and the molar ratio of these rates show the similarity in MRC-5 metabolism between the two processes. The purification of Hepatitis A from both process were remarkably similar indicating that no major changes in downstream process would be required if the virus were produced in microcarrier culture.

The specific virus production per cell in low perfusion rate microcarrier cultures (0.7 vols/day) was only 7% lower than the higher perfusion rate (1.5 vols/day) culture indicating that the perfusion rates used were not limiting to virus production. The specific virus production per cell in the microcarrier cultures was about half of that obtained for monolayer grown virus based on our best estimates of cell density. Since the perfusion rate data does not suggest a nutrient limitation, one can conclude that either all the cells did not participate in the infection or that the virus was produced but shed into the medium. In the first case, viability is believed to be high through the infection period based on a trypan blue measurements in the last run with batch refeeds (worst case) being 92% at 21 days post infection. Given the current specific virus productivity per cell for microcarrier culture, increases in overall productivity can be gained by increasing the cell density in the bioreactor through higher bead loadings. In conclusion, the aggregated microcarrier system has great potential as a scaleable process for the production of hepatitis A and other virus vaccines.

The following examples are provided to exemplify specific embodiments of this invention, but the example should not be construed as the only mode of executing this invention.

EXAMPLE 1

Hepatitis A Virus Stock Seed Manufacture

A large-scale procedure for cell and virus seed production involves the planting of MRC-5 cell monolayers in 6000 cm$^2$ NUNC CELL FACTORIES (NCFs). MRC-5 cells are grown in the NCFs to confluency. These cells may be harvested and used to plant onto microcarriers. Alternatively, the confluent cells in the NCFs are infected with virus at an MOI of about 0.1. Following infection the cells are incubated for about 28 days with weekly replacement of medium containing 10% v/v fetal calf serum. It has been found that high concentrations of serum, 2 to 10% v/v allow greater virus production than low levels, 0.5 to 2% v/v. At the end of this cycle the supernatant fluid contains large amounts of virus, in this example 10$^{7.3}$ TCID$_{50}$ per milliliter, which is harvested directly from the NCF, without cell lysis, and used as the source of virus stock seed, In this manner, the large quantities of infectious virus necessary for manufacture are obtained by a method more reproducible and facile than roller bottles or flasks, or with mechanical harvest of the cells.

EXAMPLE 2

Hepatitis A Production in an Aggregated Microcarrier System

This and the following examples illustrate the quantitive production of hepatitis A in a small scale microcarrier culture and purification of the lysate through an established HAV purification scheme. By appropriate modifications, other viruses and cell-types may be produced.

Microcarrier Spinner System, (Step 1):

The spinner system was designed to operate as a self contained unit on a cart where sampling, media changes, and infection were carried out through closed system processing using a SCD II sterile tubing welder device. The spinner vessels were custom fabricated from Bellco with a 565 ml working volume and a jacket for temperature control. The agitation system consisted of a Bellco paddle modified to a diameter of 6.6 cm. The diameter was chosen based on agitation studies involving the measurement of critical off bottom suspension stirring rates (COBSR) and calculating the hydrodynamic conditions based on that rate. A surface impeller, 4 cm long was positioned at the culture interface to provide increased oxygen transfer at higher cell densities and also assist in stripping $CO_2$. The microcarrier free effluent was removed with a ½ inch ID metal tube covered with a 10 $\mu$m mesh positioned at the desired bioreactor volume using a 50% higher flow rate than the perfusion inlet flow rate.

Microcarrier Preparation:

Glass Coated Polystyrene Microcarriers from SOLOHILL Laboratories, Inc., were used for the study. The lowest microcarrier specific gravity available from SOLOHILL, 1.02, was chosen to minimize energy input to suspend the MCs. The size range was 150–210 $\mu$m. A particle size analysis, conducted by SOLOHILL, determined the surface area and the number of beads to be 514 $cm^2/g$ and $6.6 \times 10^5$ beads per gram, respectively. The microcarrier loading for the experiment was selected at 35.4 g/liter.

The MCs were placed in the siliconized 500 ml jacketed spinners, suspended in WFI water and autoclaved for 30 minutes at 122° C. The MCs were then washed 3 times with modified William's Media E, with 2 mM glutamine, without serum.

EXAMPLE 3

Cell Expansion/Inoculation of Spinners, (Step 2):

Fourteen NCFs were planted with MRC-5 cells. Twelve NUNC CELL FACTORIES (NCFs) were harvested and used to plant two COSTAR CUBE bioreactors. The remaining 2 NCFs were harvested and used as inoculum for the microcarrier spinners. The cells were centrifuged for 10 minutes at 300×g and resuspended in 10% iron supplemented calf serum (FeCS), 90% modified Williams Media E with 2 mM Glutamine. No antibiotics were used in the exeriment. The cells are attached at about 8 cells/bead in 1% FeCS, pH 7.7, at 37° C. Within 3 hours all the cells attach and the media is brought to 10% FeCS to begin the growth phase.

According to a Poisson distribution, only 5 cells per bead should be required to insure that at least one cell is attached to each bead through random encounters between the cells and beads. We have found that under the attachment conditions specified above, 5 cells per bead often results in some microcarriers (MCs) without cells. These microcarriers remained as single MCs through the cultivation which further substantiated that the aggregation phenomena occurs through cell to cell contact and not cell to MC content contact. In this example the cell per bead ratio was 8.2 and all MCs were observed to have at least one cell attached after 3 hours (cells are still rounded up and therefore visible on the opaque MCs). The difference in the minimal cell/bead ratio may be due to aggregation of some of the cells at the planting stage, resulting in a drop in the predicted cell-to-bead ratio. Routine experimentation, however, allows optimization of the attachment conditions for this system.

Figure 1:
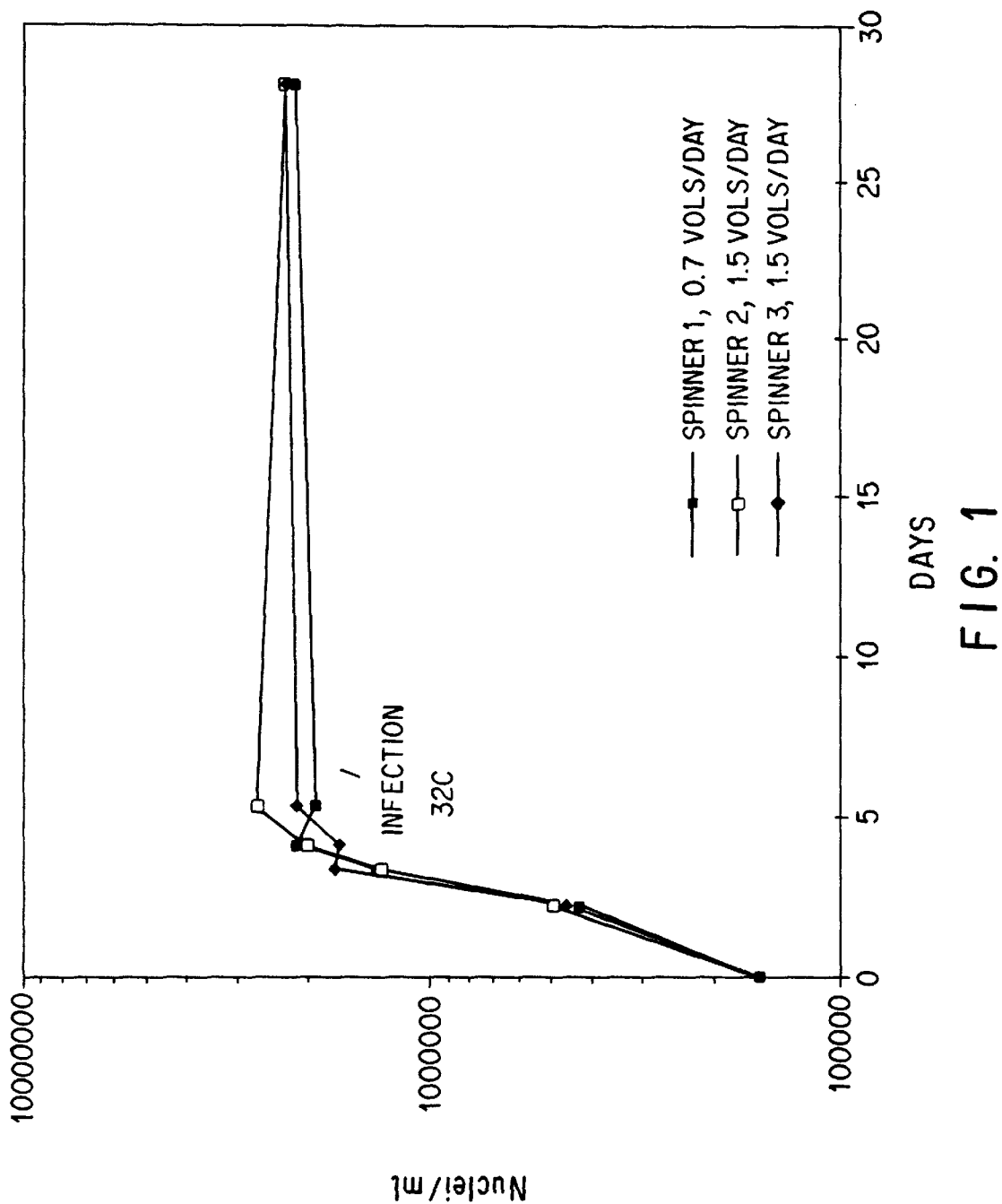
FIG. 1. Cell density for the growth phase and harvest of hepatitis A virus grown on MRC-5 and SOLOHILL glass microcarriers.

In this experiment, the cell density at plant was $1.5 \times 10^5$ cells/ml which corresponds to 8600 cells/$cm^2$ MC. By day 2 small aggregates of 2–5 MCs formed which grew to 10–30 MCs by day 5. Subsequently, some of the 10–30 MC aggregates combined to form ~50 MC aggregates. It is quite clear that cell growth occurs through the aggregation process. No single MCs were present in the culture and cell growth within the void space between the MCs was apparent. The cell growth profile, illustrated in FIG. 1 indicates the cultures reached a cell density of 2–3 MM cells/ml on day 5. Nuclei counts on day 6 were lower since the larger aggregates became lodged in a constriction in the sample line. Since the particle concentration decreases about 50 fold due to aggregation, the culture changes from rather opaque with the single MCs to quite translucent. Thus, monitoring the progress of the culture on-line with a turbidity probe is possible. No floating cells due to cell sloughing were observed in effluent samples during the 28 day run. The nuclei counts from the bioreactor harvest at the end of the run also indicate that the culture remained stable throughout the infection period. We have found that the aggregates were very stable once formed, even under extremes in pH, presence of EDTA, and higher agitation rates. Since the aggregates readily breakup in the presence of trypsin, the aggregates are most likely stabilized by the creation of a extracellular matrix composed of collagens secreted by the cells.

EXAMPLE 4

Perfusion, (Step 3):

The cultures were initially grown in batch mode for 2 days using bottled media and UV irradiated serum. On day two, perfusion was initiated using bag media obtained from JRH with modified William's Media E combined with FeCS. The bag lot was comprised of 10 and 20 liter Stedim bags; both the Modified Williams Media E and non irradiated FeCS serum lots were accepted by Merck for production use. Before and after the run the growth of MRC-5 cells in T-flasks was compared using the serum supplemented bag media and bottled media with irradiated serum added as a control. Glucose, lactate, and ammonia were identical, demonstrating 6 month stability for the FeCS/basal media mixture from the date the serum and media were combined. During the experiment, the medium was supplemented with bicarbonate to a final concentration of 3.7 g/liter to maintain the pH above 7.3.

The target perfusion rates were 0.7 volumes per day (spinner 1) and 1.5 volumes per day (spinners 2 & 3) based on a 565 ml bioreactor volume. However, the microcassette Watson Marlow Pumps we used did not precisely control the flowrate at a set RPM, particularly after the tubing was moved. The rates were periodically measured and the measured rates listed below were used in all calculations. The average perfusion rates during the infection were 0.76, 1.51, and 1.51 for the 3 spinners respectively. Inline rotometers and wider bore tubing (lower RPMs) would assist in the efficiency of this system. Note also that the rates were corrected when perfusion was interrupted due to failure to change the bags in time, see Table I:

TABLE I

Measured Perfusion Rates: Bioreactor Volumes/Day

| Culture Age Days | Spinner #1 Volumes/Day | Spinner #2 Volumes/Day | Spinner #3 Volumes/Day |
|---|---|---|---|
| 2 | 0.5 | 1.2 | 1.2 |
| 3 | 0.5 | 0.6 | 0.6 |
| 4 | 0.5 | 1.2 | 1.2 |
| 5 | 0.5 | 1.2 | 1.2 |
| 6 | 0.5 | 1.2 | 1.2 |
| 7 | 0.64 | 1.84 | 1.84 |
| 8 | 0.7 | 2.1 | 2.1 |
| 9 | 0.7 | 2.1 | 2.1 |
| 10 | 0.7 | 1.67 | 1.67 |
| 11 | 0.7 | 1.6 | 1.6 |
| 12 | 0.7 | 1.27 | 1.27 |
| 13 | 0.7 | 1.3 | 1.3 |
| 14 | 0.7 | 1.3 | 1.3 |
| 15 | 0.8 | 1.4 | 1.4 |
| 16 | 0.8 | 1.4 | 1.4 |
| 17 | 0.8 | 1.4 | 1.4 |
| 18 | 0.8 | 1.4 | 1.4 |
| 19 | 0.8 | 1.4 | 1.4 |
| 20 | 0.8 | 1.4 | 1.4 |
| 21 | 0.8 | 1.4 | 1.4 |
| 22 | 0.8 | 1.4 | 1.4 |
| 23 | 0.8 | 1.4 | 1.4 |
| 24 | 0.8 | 1.4 | 1.4 |
| 25 | 0.9 | 1.86 | 1.86 |
| 26 | 0.8 | 1.4 | 1.4 |
| 27 | 0.8 | 1.4 | 1.4 |
| 28 | 0.8 | 1.4 | 1.4 |

Perfusion Rate: 1.5 volumes/day = 565 ml/24 hours = 23.5 ml/hr

Figure 2:
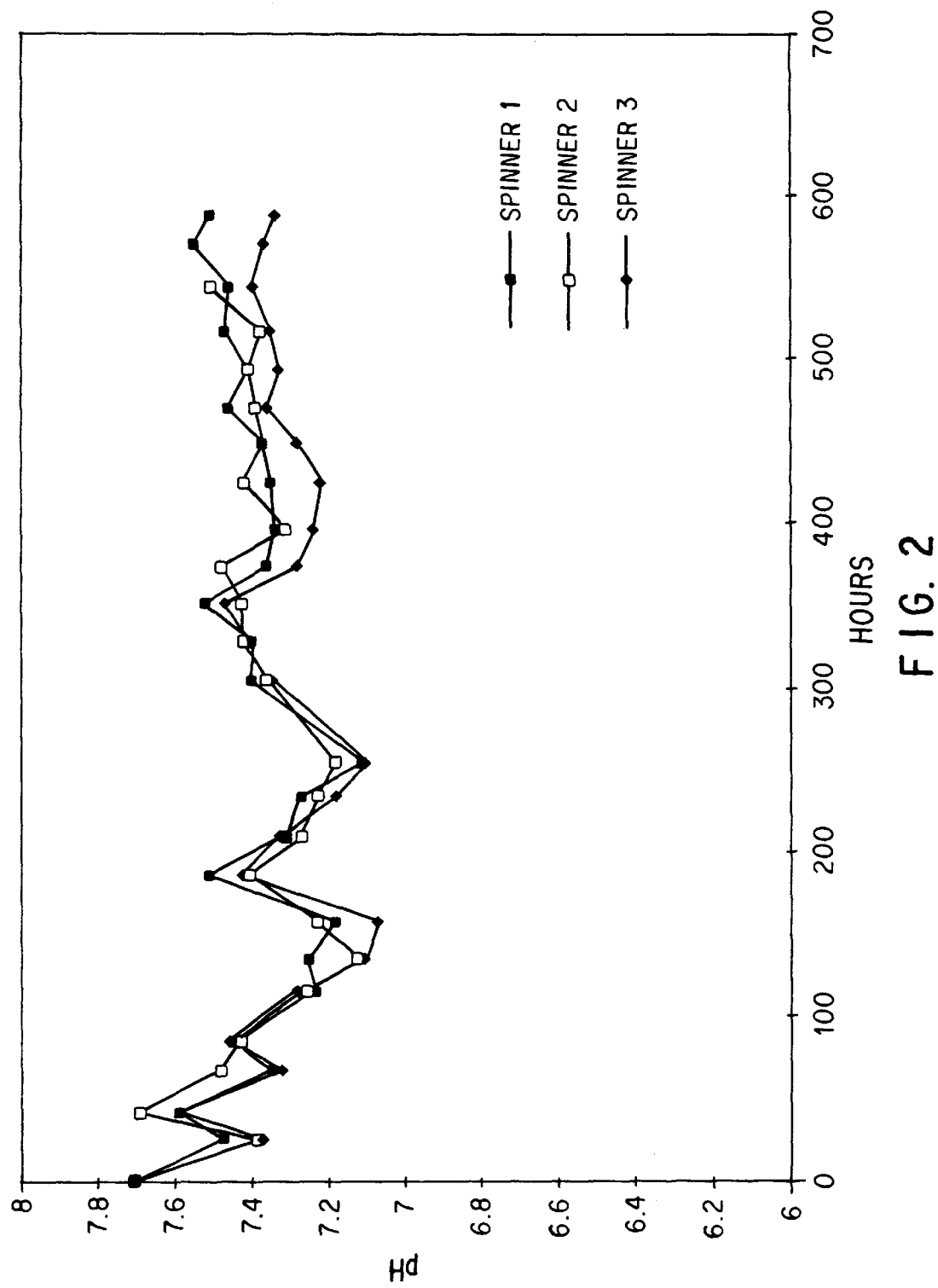
FIG. 2. The pH profile for perfused microcarrier spinner cultures for the growth phase and harvest of hepatitis A virus grown on MRC-5 cells and SOLOHILL glass microcarriers.

The optimum pH for MRC-5 cells is reported in the literature to be pH 7.7, and a complete cessation of growth was shown to occur at pH 7.2 (Forestell, S. et a., Biotechnol. Bioneg. 39:305–313, 1992). The production COSTAR CUBES are controlled at a pH set point of 7.3 throughput the cultivation. Since there is no pH control in the spinner flasks, maintaining a pH above 7.3 relied on perfusion to remove the lactic acid and the surface impeller to increase the stripping of the CO2 from the liquid phase. The pH profile provided in FIG. 2 illustrates the drop in pH through the first 150 hours. At that time sodium bicarbonate was added to subsequent media bags to increase the concentration from 2.2 g/liter to 3.7 g/liter for added buffering capacity.

One of the objectives of this experiment was to create a microcarrier culture with a similar density as that estimated for growth in a production scale, monolayer cell culture system. One such system utilizes COSTAR CUBE bioreactors. In what follows, we compare the metabolic profiles of glucose, lactate, and ammonia in a COSTAR CUBE based process and in our microcarrier process. The cell mass in non-infected production COSTAR CUBES was measured to be $1.6 \times 10^6$ cells/ml on the day of infection and $3.0 \times 10^6$ after 28 days. Since the glucose uptake rate continues to rise just after the infection time it is likely that much of the cell density increase (1 doubling) occurs then and this cell density is maintained in the COSTAR CUBE over the rest of the infection. The cell density in an infected COSTAR CUBE is expected to be between these two cell densities and is most likely over $2 \times 10^6$ cells/ml. Based on the estimates, we conclude that the microcarrier cultures and the COSTAR CUBE bioreactor are in the same cell density range. The perfusion rates for the microcarrier cultures range from 0.7 to 1.5 bioreactor volumes per day which encompasses a rate of 1.3 volumes per day used in a COSTAR CUBE based culture process. At similar cell densities and perfusion rates one would expect the metabolic profiles to be similar between the two processes if cell metabolism was similar as well.

Figure 3:
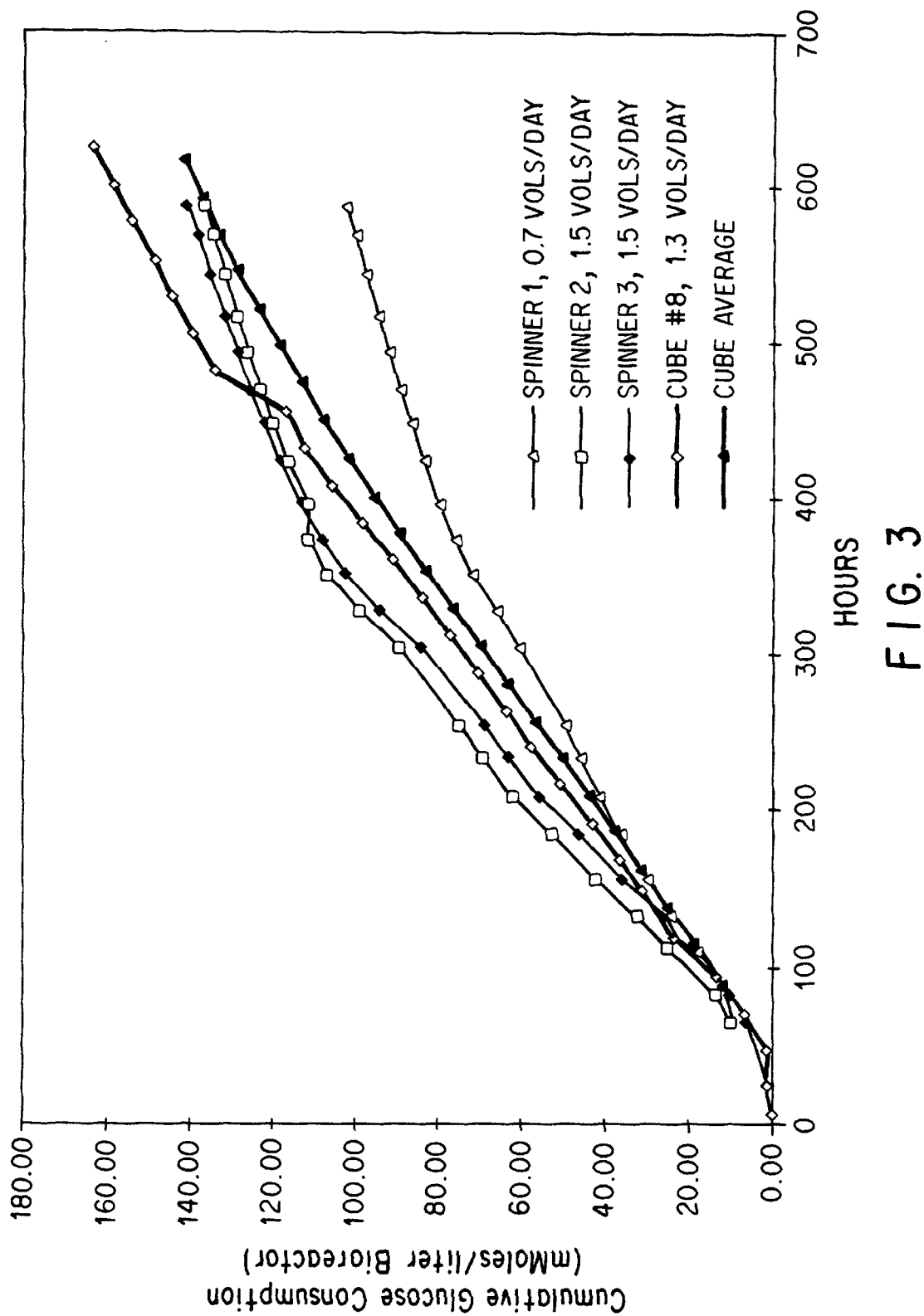
FIG. 3. Cumulative glucose consumption for perfused microcarrier spinner cultures as compared with monolayer cell culture for the growth phase and harvest of hepatitis A virus grown on MRC-5 cells and SOLOHILL glass microcarriers, and COSTAR CUBE surfaces, respectively.
Figure 4:
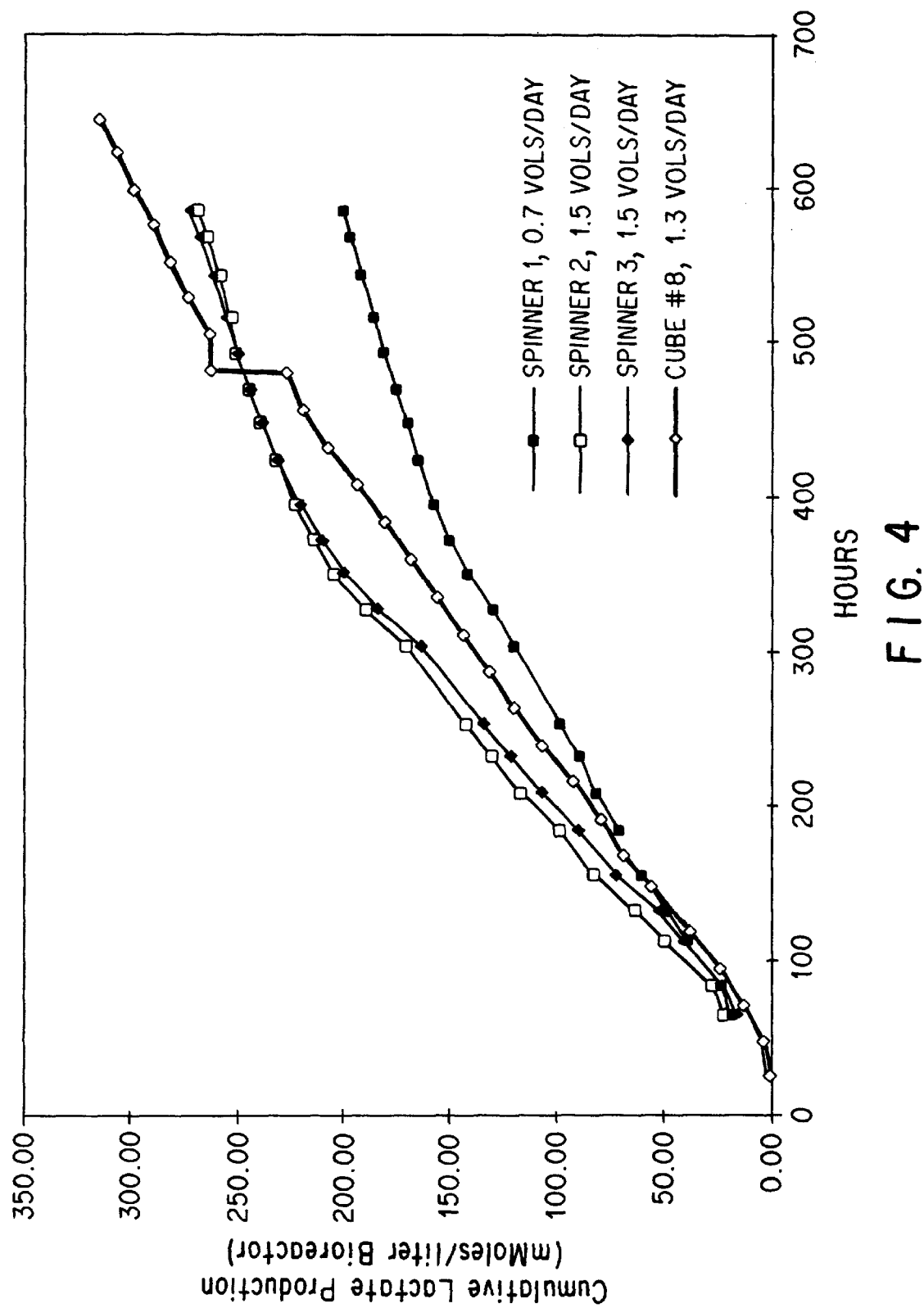
FIG. 4. Cumulative lactate production for perfused microcarrier spinner cultures as compared with monolayer cell culture for the growth phase and harvest of hepatitis A virus grown on MRC-5 cells and SOLOHILL glass microcarriers, and COSTAR CUBE surfaces, respectively.
Figure 5:
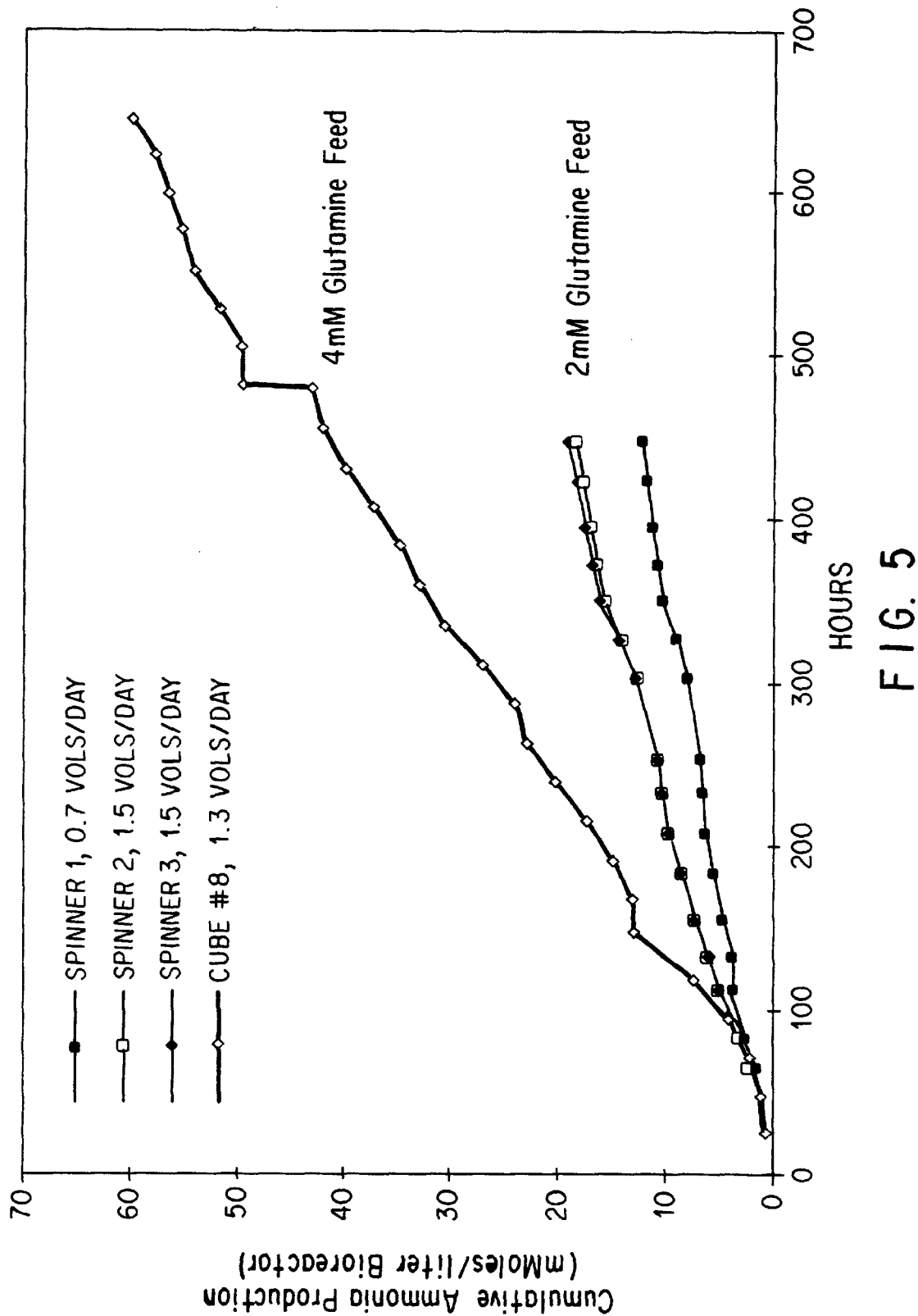
FIG. 5. Cumulative ammonia production for perfused microcarrier spinner cultures as compared with monolayer cell culture for the growth phase and harvest of hepatitis A virus grown on MRC-5 cells and SOLOHILL glass microcarriers, and COSTAR CUBE surfaces, respectively.
Figure 6:
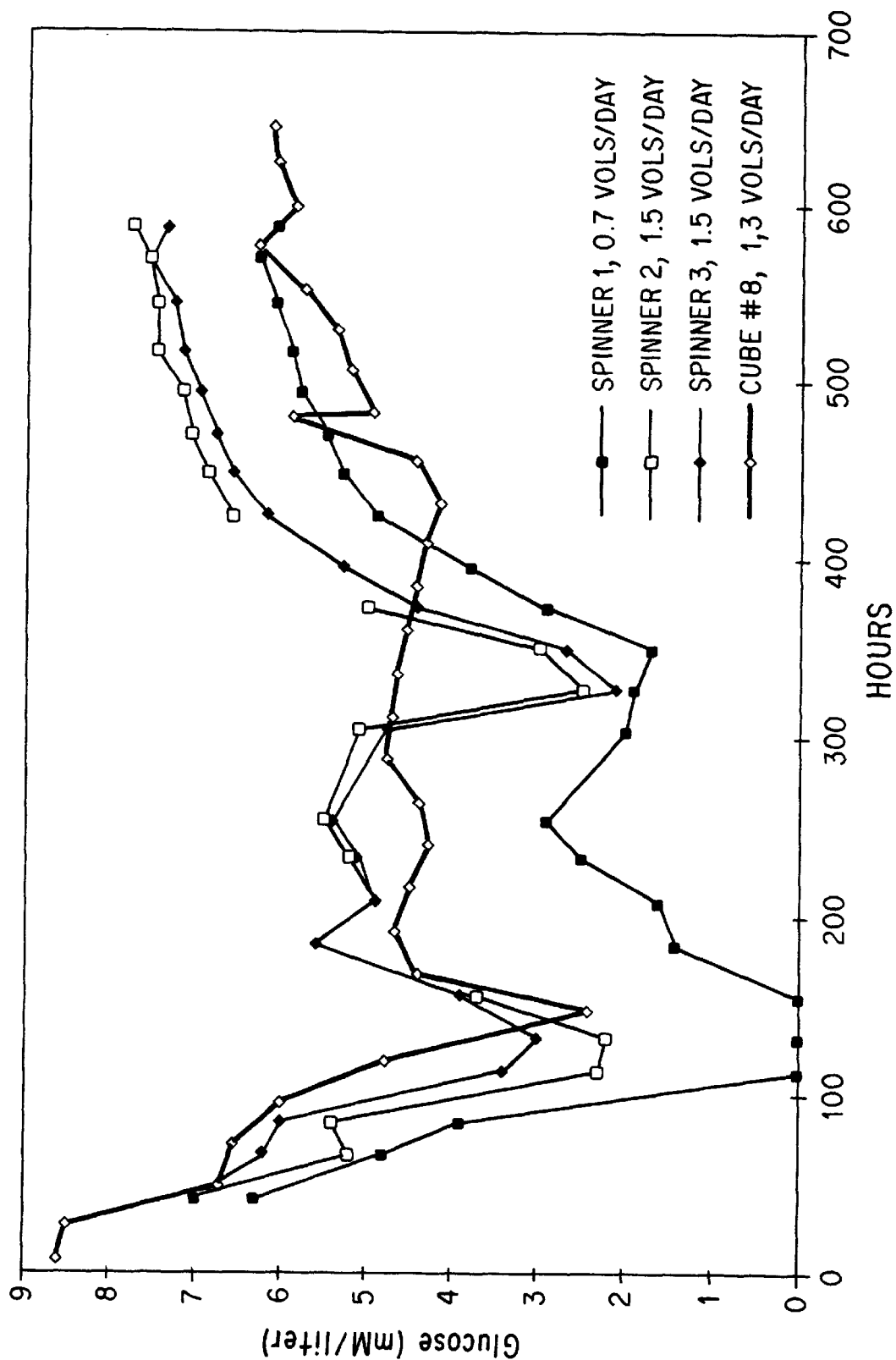
FIG. 6. Glucose consumption profile for perfused microcarrier spinner cultures as compared with monolayer cell culture for the growth phase and harvest of hepatitis A virus grown on MRC-5 cells and SOLOHILL glass microcarriers, and COSTAR CUBE surfaces, respectively.
Figure 7:
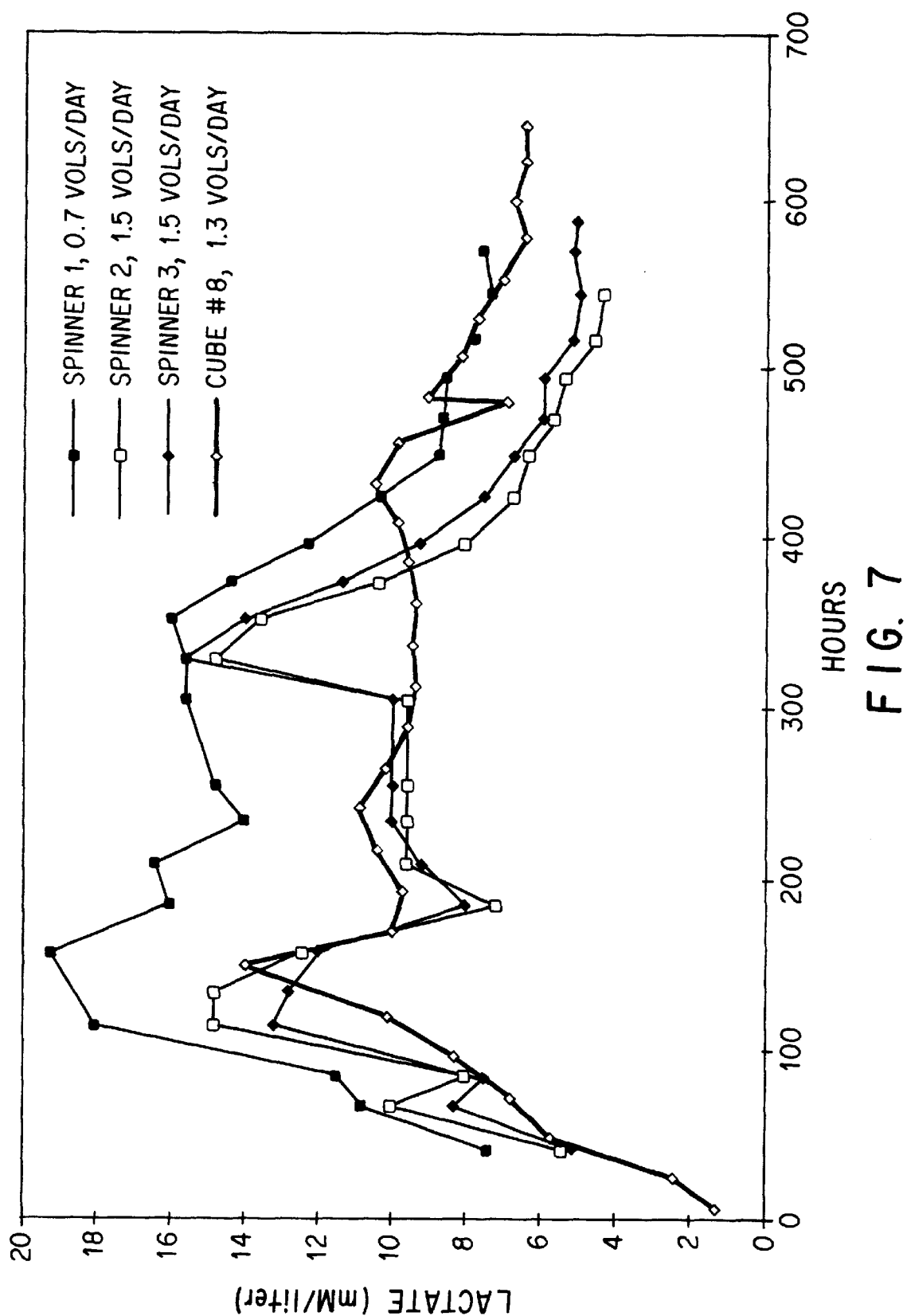
FIG. 7. Lactate production profile for perfused microcarrier spinner cultures as compared with monolayer cell culture for the growth phase and harvest of hepatitis A virus grown on MRC-5 cells and SOLOHILL glass microcarriers, and COSTAR CUBE surfaces, respectively.
Figure 8:
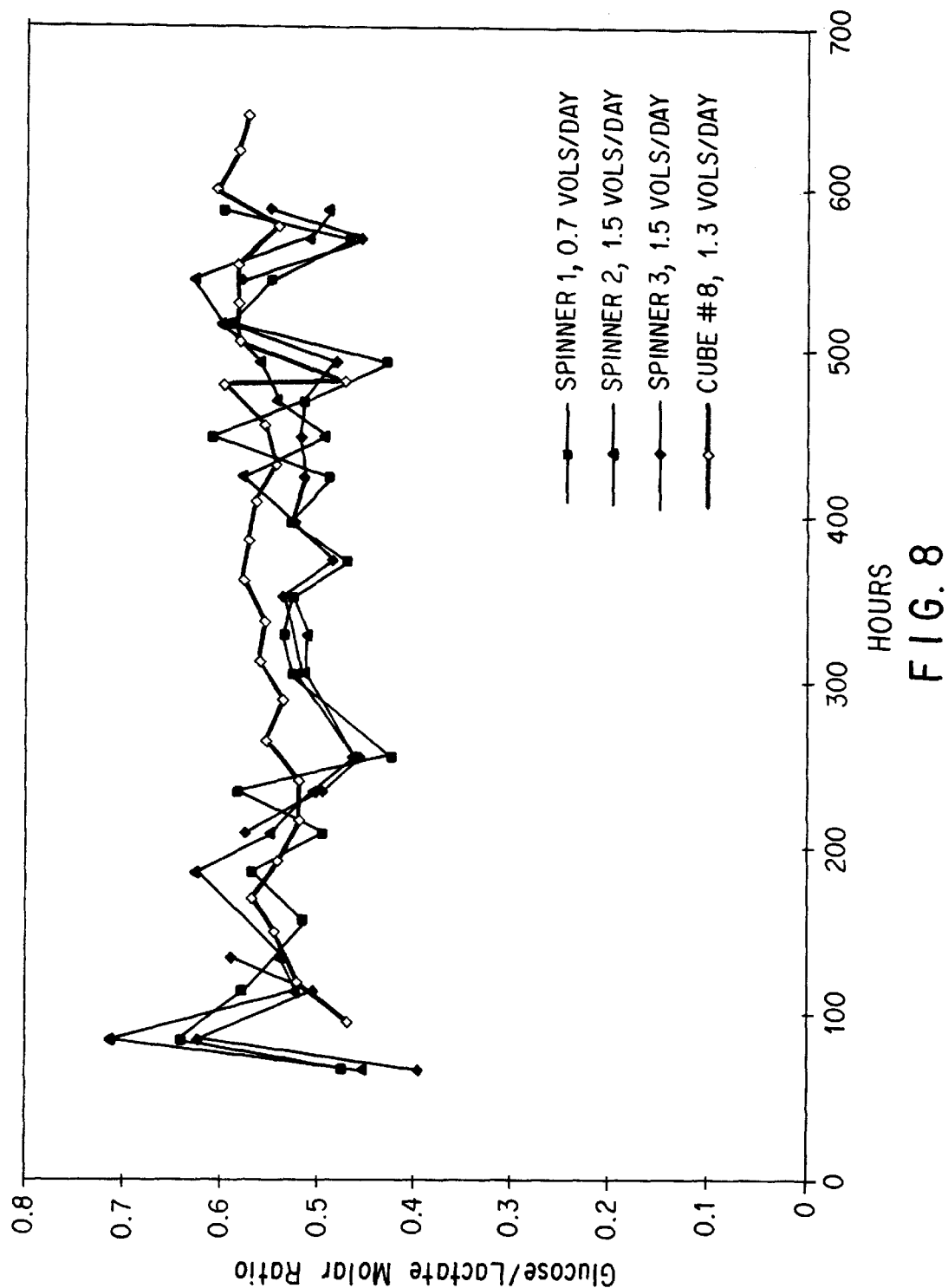
FIG. 8. Ratio of glucose consumption and lactate production for perfused microcarrier spinner cultures as compared with monolayer cell culture for the growth phase and harvest of hepatitis A virus grown on MRC-5 cells and SOLOHILL glass microcarriers, and COSTAR CUBE surfaces, respectively.

The cumulative amount of glucose utilized, lactate produced and ammonia produced over the course of an infection for both systems is illustrated in FIGS. 3, 4 and 5, respectively. The cumulative amount was calculated by mass balance given the perfusion rate and concentration profile over time. In FIG. 3 the cumulative glucose is given for the 3 microcarrier cultures, a representative COSTAR CUBE reactor, and the average cumulative glucose from 18 COSTAR CUBE production lots. The plot illustrates that the production COSTAR CUBE data is bracketed by the microcarrier data at the higher and lower perfusion rates as expected if metabolism was similar. The figure also illustrates that the representative COSTAR CUBE behaves similarly to the average COSTAR CUBE data with the exception of the shift at about 450 hours which is likely due to a disruption of the perfusion operation. The cumulative lactate profile again shows a similar trend with the accumulation of lactate in the COSTAR CUBE process being between the microcarrier process at the higher and lower perfusion rates. The specific glucose rate (mMoles glucose consumed/liter/hr) which corresponds to the slope of the cumulative glucose versus time plot, increases with increasing perfusion rates through the first 400 hours of the run. This may be indicative of the difference in glucose concentration affecting the rate at which the glucose is metabolized. In FIGS. 6 and 7 the difference in glucose and lactate concentration in the bioreactor between the 0.7 vol/day and 1.5 vol/day microcarrier cultures is apparent. Another reason for the difference may be small differences in cell density in the bioreactors. The ratio of the glucose and lactate rates illustrated in FIG. 8 indicates a stoichiometric conversion of glucose to lactate through the glycolytic pathway for both processes.

The cumulative production of ammonia illustrated in FIG. 5 shows a dramatic difference in glutamine metabolism when a lower glutamine concentration is used. By error, in one COSTAR CUBE experiment, the concentration of glutamine was doubled due to the inadvertent addition of glutamine to glutamine containing media. Based on this data it is likely that glutamine is limiting in the 2 mM concentration cultures. Glutamine typically enters the tricarboxyllic acid cycle (TCA) through α-ketoglutarate with the loss of one amino group (and transamination of the second amino group). Assuming all the glutamine fed to the bioreactor is converted 1:1 to ammonia, the ammonia accumulation rate would be 0.071 mM/liter/hr for 1.5 vols/day and 0.033 mM/liter/hr for 0.7 vols/day. These rates are close to the average rate seen for these cultures. It also can be seen that at the same feed concentration but at a higher perfusion rate, the utilization rate based on ammonia production increases. This effect was also seen with glucose metabolism and indicates a concentration dependent utilization rate which as been reported for other cell lines.

EXAMPLE 5

Infection, (Step 4):

On day 7 the cultures were infected with HAV Stock Seed prepared, for example, as described above in Example 1, at a target MOI of 0.1 (i.e.: 1 virion per 10 cells in the bioreactor as quantified by nuclei counts). Subsequently, the stock seed titer was found to be 7.19 logs instead of 7.4 logs resulting in an actual MOI of 0.062. The temperature was lowered to 32° C. about 5 hours before the infection. Perfusion mode was resumed 2 hours after infection.

Culture pH was measured with a Corning-Ciba Blood Gas Analyzer. Care was exercised to insure the pH was not altered by stripping the $CO_2$ during sampling. Glucose, lactic acid, and ammonia were analysed using a Kodak Biolyzer. Samples were diluted with WFI when required; in the case of ammonia, the concentration was corrected for the ammonia concentration in the WFI. Cell density was quantified by the method of Sanford et al., (*J. Nat. Cancer Inst.*, 11:773–795, 1951) where nuclei are released and stained with 0.1% (w/v) crystal violet and 0.1 mM citric acid. Sampling of the culture for cell counts was terminated on day 6 since the aggregates were getting hung up in a constriction in the sample line. Media effluent sampling was performed daily.

Figure 9:
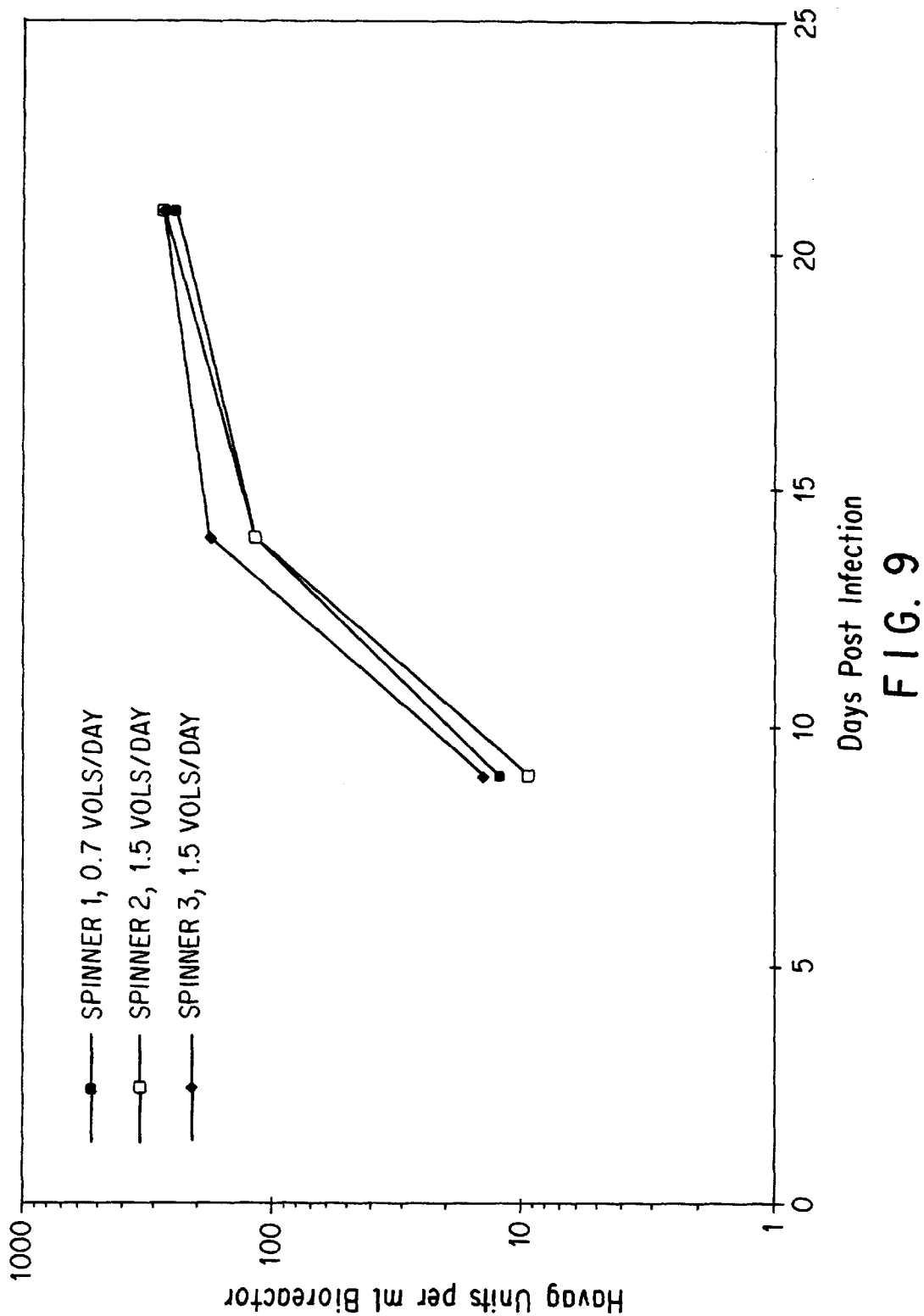
FIG. 9. Hepatitis A virus growth curve for perfused microcarrier spinner cultures on SOLOHILL glass microcarriers.

A virus growth curve from day 9 to day 21 post infection is provided in FIG. 9. The Havag (HAV antigen by ELISA assay) units/ml bioreactor were obtained by correcting the titer for the dilution of the sample during the harvest procedure. The virus growth rate appears to be substantially lower in the third week of the infection. Another possibility is that the culture peaked earlier than 21 days and virus was being shed into the media by day 21. From NCF experiments we knew that the virus can be harvested from the cells at day 21 post infection and harvested from the media at day 28. The latter procedure is still used to generate stock seed in NCFs (see Example 1).

A comparison of virus production between the COSTAR CUBE process and the microcarrier process is provided in Table IIa and IIb:

TABLE IIa

Havag Yield per Liter Bioreactor Volume at 21 Days Post Infection

|  | Perfused Production Cube | Perfused Microcarrier Cultures | | |
| --- | --- | --- | --- | --- |
|  | Bioreactor 1.3 vols/day | Spinner #1 0.7 vols/day | Spinner #2 1.5 vols/day | Spinner #3 1.5 vols/day |
| Total Havag Units Produced | $1.9 \times 10^7$ | $1.34 \times 10^5$ | $1.51 \times 10^5$ | $1.52 \times 10^5$ |
| Bioreactor Volume | 28 liters | 565 ml | 565 ml | 565 ml |
| Havag Units/ml Bioreactor | 695 | 237 | 268 | 269 |

TABLE IIb

Havag Yield per Cell at 21 Days Post Infection

|  | Perfused Production Cube | Perfused Microcarrier Cultures | | |
| --- | --- | --- | --- | --- |
|  | Bioreactor 1.3 vols/day | Spinner #1 0.7 vols/day | Spinner #2 1.5 vols/day | Spinner #3 1.5 vols/day |
| Havag Units/ml Bioreactor | 695 | 237 | 268 | 269 |
| Cells/ml Bioreactor | Estimated* $2.4$–$3.0 \times 10^6$ | $2.21 \times 10^6$ | $2.34 \times 10^6$ | $2.36 \times 10^6$ |
| Havag Units per $10^6$ cells | 229–286 | 107 | 115 | 114 |

*Cell estimate based on a measured non-infected cell density of $2.5 \times 10^5$ cells/cm$^2$ after 21 days in the COSTAR CUBE corresponding to 3MM cells/ml and a lower estimate on $2.0 \times 10^5$ cells/cm$^2$.

Two comparisons are made: A volumetric yield, (Havag per liter bioreactor) and a cellular specific yield, (Havag per cell). The Havag yield per liter bioreactor provides a direct yield calculation of bioreactor productivity. Since the cell densities are similar between the various microcarrier reactors and similar to the estimated cell density in the COSTAR CUBE production bioractor, a direct comparison of productivity can be made using this yield. The production COSTAR CUBE reactor yield is the average total Havag harvested for several COSTAR CUBE cultivations divided by the 28 liter bioreactor volume. The productivity of the 3 microcarrier spinners were quite similar with the lower perfusion rate culture (Spinner #1) showing only a 12% decrease in yield. The yield from the microcarrier culture was 38% of that obtained from the COSTAR CUBE process. Similar productivities could be obtained by increasing the bead loading to drive up the cell density in the microcarrier culture to more than 2 times the cell density used here.

The Havag units per cell data for the COSTAR CUBE was estimated based on the estimated cell density in the COSTAR CUBE as discussed earlier. The cell densities for the spinners are a direct measure of the nuclei released during the harvest of each bioreactor at 21 days. Since there were slightly less cells measured in the low perfusion rate bioreactor, the per cell yield is only 7% lower than the other spinners (versus 12% on a volumetric basis). This indicates that the lower perfusion rate was only slightly limiting in virus production. The microcarrier cell yields are about 40–50% of the estimated yields per cell for the COSTAR CUBE which is in rough agreement with the volumetric yields since the cell densities are approximately similar in the bioreactors.

EXAMPLE 6

Harvest, (Step 5):

In the following analysis, we used two harvest procedures: a small 5 ml harvest at 9 and 14 days post infection and a full bioreactor harvest on day 21 post infection.

For the small scale samples, the 5 ml aliquot of aggregated MCs was washed twice with PBS, and suspended in 0.1% triton lysis buffer. The aggregates were broken up by fluid shear with a pipetman and sampled to count nuclei. The nuclei were visualized by diluting a 200 $\mu$l sample 1:1 with 0.1% crystal violet/0.1 mM citric acid solution. The lysate was then centrifuged at 300×g to remove nuclei and aliquoted for EIA assay.

For the bioreactor harvest, the media was removed by aspiration and the aggregates washed twice with a bioreactor volume of PBS. One bioreactor volume of 0.1% Triton lysis buffer was then added to the aggregates and recycled through a set of $\frac{1}{16}$", $\frac{1}{32}$", and $\frac{1}{64}$" orifices in series at a flowrate of about 700 ml/min. After 15–30 minutes of recirculation, the MCs (and small 1–3 MC aggregates) were allowed to settle and the MC free lysate was removed. A second bioreactor volume of 0.1% Triton was added to the MCs, recycled through the orifices for 15–30 minutes and pooled with the 1st lysate. The pool was sampled to quantify nuclei (see above procedure), EIA, and HPSEC. The microcarriers were microscopically observed to verify removal of cell mass.

The aggregates were quite stable during the 2 rinses with PBS stirred at over 3 fold the operating agitation rate (75 vs 25 RPM). From small scale harvests, we established that the aggregates would be difficult to break up even in the presence of triton lysis buffer. Therefore a series of orifices were used to simulate the fluid shear generated by a pipetman on the small scale. The recirculation time of about 15 minutes per wash at a flowrate of ~700 ml/min seemed to be enough to get adequate breakage; visual observation of the lysate showed single MCs and nuclei. The recirculation time reported herein is probably not optimal but optimal recirculation will easily be established by routine experimentation based on the instant disclosure. An advantage of the procedure is that it serves to release nuclei for quantification of the cell density at the time of harvest. The main difference between the lysate from monolayer culture and the microcarrier lysate is the need to filter out the microcarriers and nuclei before filtration of the smaller debris for passage through the 0.2 μm filters.

EXAMPLE 7

Purification, (Step 6)

Any of a number of known procedures for purification of the HAV produced according to the above described process may be utilized to prepare purified HAV. Below, we provide one procedure which reproducibly provides HAV of superior purity.

1. Lysate Filtration/BENZONASE:

About 800 ml of lysate was filtered through a Durapore 5 μm filter to remove nuclei and MCs followed by a 0.2 μm filter to remove smaller debris. The COSTAR CUBE lysate was filtered through only a 0.2 μm filter; subsequently the COSTAR CUBE and microcarrier lysates were treated identically. The 0.1% triton buffer was supplemented with 2M $MgCl_2$ to a final concentration of 2 mM. BENZONASE, a commercially available nuclease produced as a recombinant protein by Nycomed Pharma A/S (Denmark), (58 μl/liter lysate) was added to each lysate and incubated overnight at room temperature with agitation.

2. Capture Column:

About 800 ml of BENZONASE endonuclease treated lysate was filtered through a 0.2 μm filter and loaded by gravity (2 meter height differential) onto a 2.6 cm diameter capture column containing 54 ml of Toyopearl 650M resin. The column was washed with 0.03M NaCl for 20 column volumes and the product was eluted by gravity at ~6 ml/min using a step change to 0.35M NaCl.

3. PEG Precipitation and Solvent Extraction:

After storage at 4° C. overnight, the eluted capture column product (~30 ml) was incubated with 4.5% PEG and 0.42M salt solution at 4–8° C. to precipitate the Hep A and centrifuged at 1000×g. The pellet was resuspended in phosphate saline buffer with EDTA, (PNE), combined with 2 parts chloroform:isoamyl alcohol 24:1 mixture, manually shaken for 3 minutes, and centrifuged at 3000×g. The aqueous phase (~7 ml) was removed and the solvent was reextracted with 3.45 ml PNE buffer. The pools were combined as the solvent extracted product.

4. EIA, HPSEC and SDS PAGE Analysis:

EIA analysis and HPSEC assay (Rainin HPLC system with TSK-Gel G4000pw size exclusion column) were run on samples from each step in the purification process. The filtered lysate and nuclease treated lysate were run at 260 nm while others were run at 214 nm. The SDS PAGE analysis of the solvent extracted product was run on a 12% gel.

TABLE 3

Purification EIA Step Yields

| Step | Full Scale Process | Cube #8 Lysate | Microcarrier Lysates | | |
|---|---|---|---|---|---|
| | | | #1 | #2 | #3 |
| Filtered Lysate | 88 | 99 | 84 | 78 | 80 |
| Nuclease Treatment | 100 | 89 | 100 | 88 | 91 |
| Capture Column | 62 | 60 | 55 | 73 | 72 |

TABLE 3-continued

Purification EIA Step Yields

| Step | Full Scale Process | Cube #8 Lysate | Microcarrier Lysates | | |
|---|---|---|---|---|---|
| | | | #1 | #2 | #3 |
| PEG | 108 | 82 | 88 | 84 | 88 |
| Solvent Extraction | 54 | 46* | 64 | 72 | 77 |
| Overall Thru Extraction | 32 | 20 | 26 | 30 | 35 |

*EIA data for this yield were derived from 1 month old samples

TABLE 4

Purification: Relative Hepatitis A Area % by HPSEC

| Input Source | PEG Precipitate 214 nm, Area % | AQX Product, 214 nm, Area % | AQX Product, BSA Peak Corrected 214 nm, Area % |
|---|---|---|---|
| Cube #8 Lysate | 35% | 90% | 98% |
| Microcarrier #1 | 3% | 55% | 93% |
| Microcarrier #2 | 41% | 71% | 98% |
| Microcarrier #3 | 44% | 73% | 97% |
| Production Average Lots 18–26 | 27.9% SD 3.5% | 68.3% SD 6.9% | |

Figure 10:
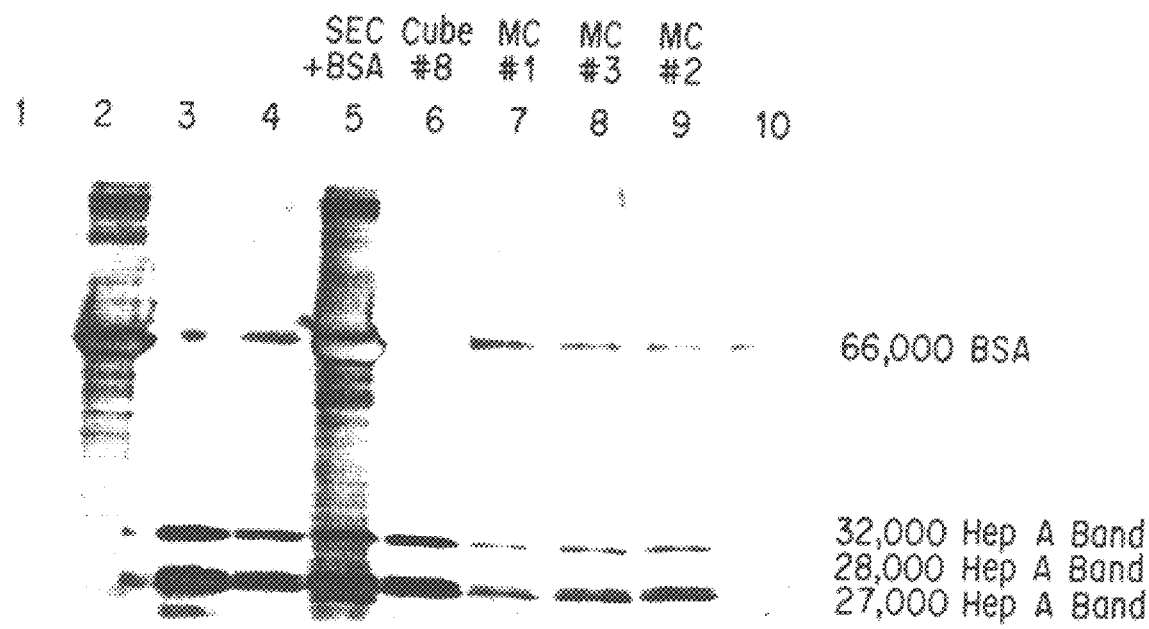
FIG. 10. SDS PAGE of solvent extracted hepatitis A virus grown in perfused microcarrier spinner cultures on SOLOHILL glass microcarriers.
Figure 11:
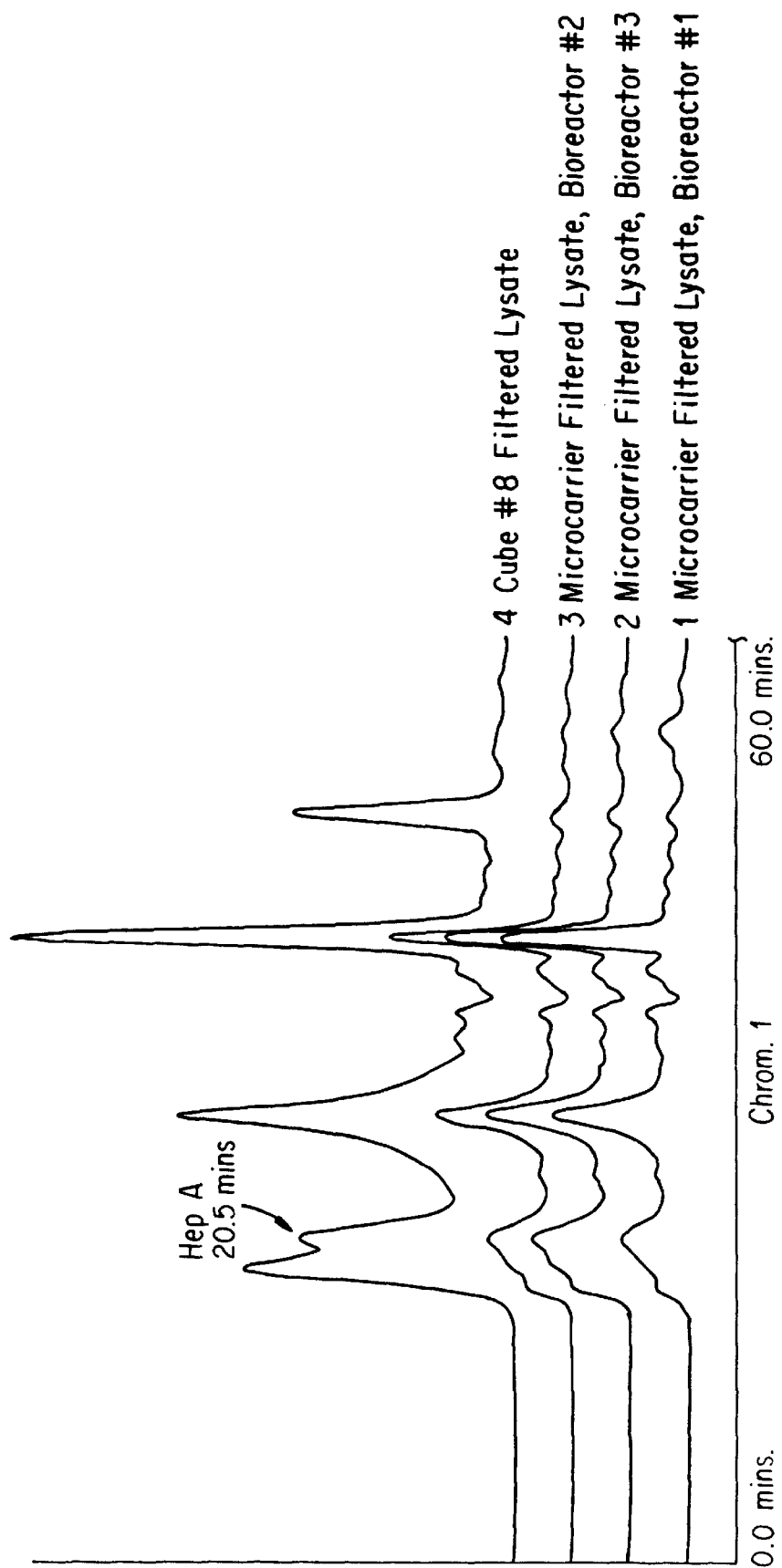
FIG. 11. HPSEC profile for filtered lysates at 260 mm for perfused microcarrier spinner cultures as compared with monolayer cell culture for hepatitis A virus grown on MRC-5 cells and SOLOHILL glass microcarriers, and COSTAR CUBE surfaces, respectively.
Figure 12:
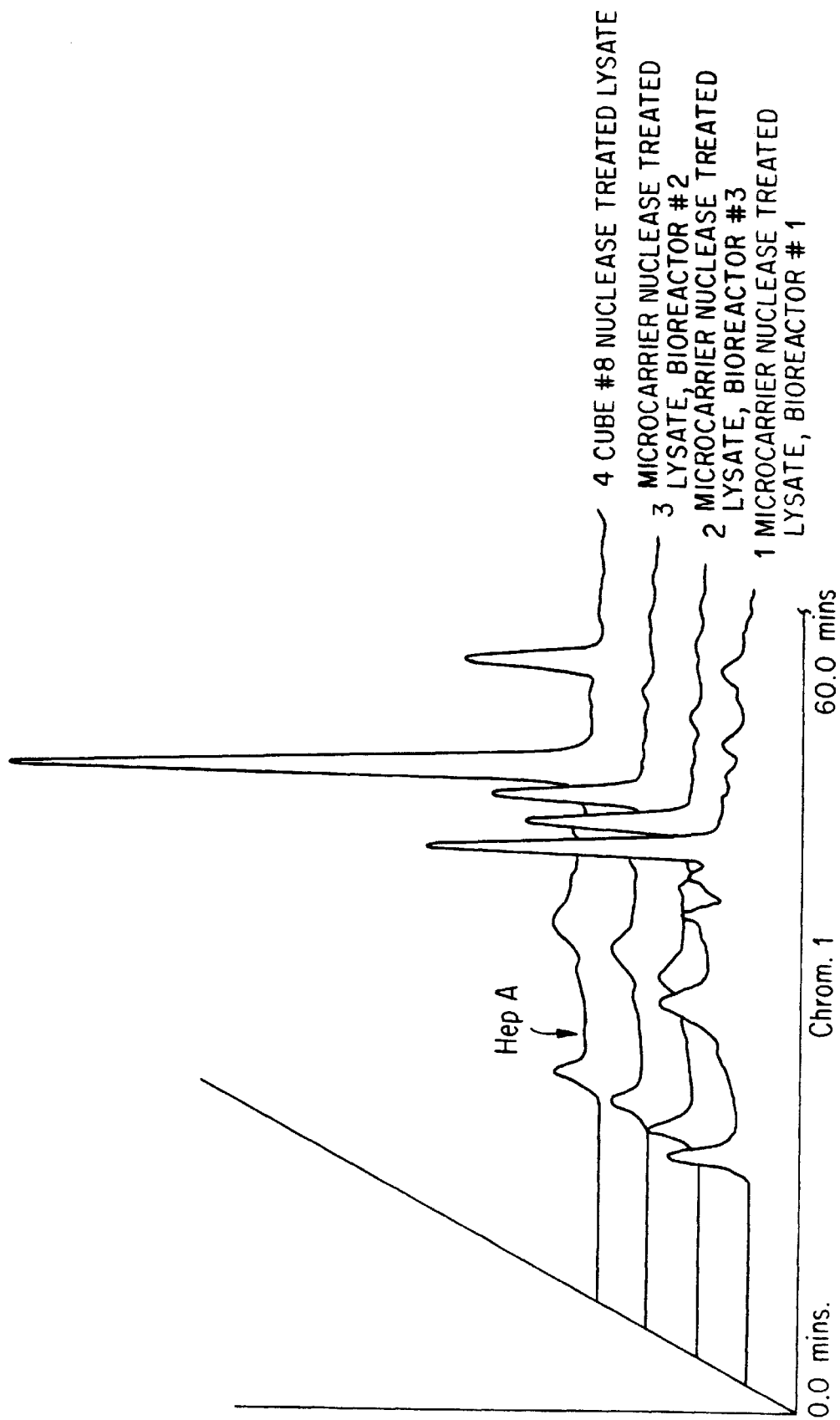
FIG. 12. HPSEC profiles at 260 mm for nuclease treated lysates from perfused microcarrier spinner cultures as compared with monolayer cell culture for hepatitis A virus grown on MRC-5 cells and SOLOHILL glass microcarriers, and COSTAR CUBE surfaces, respectively.
Figure 13:
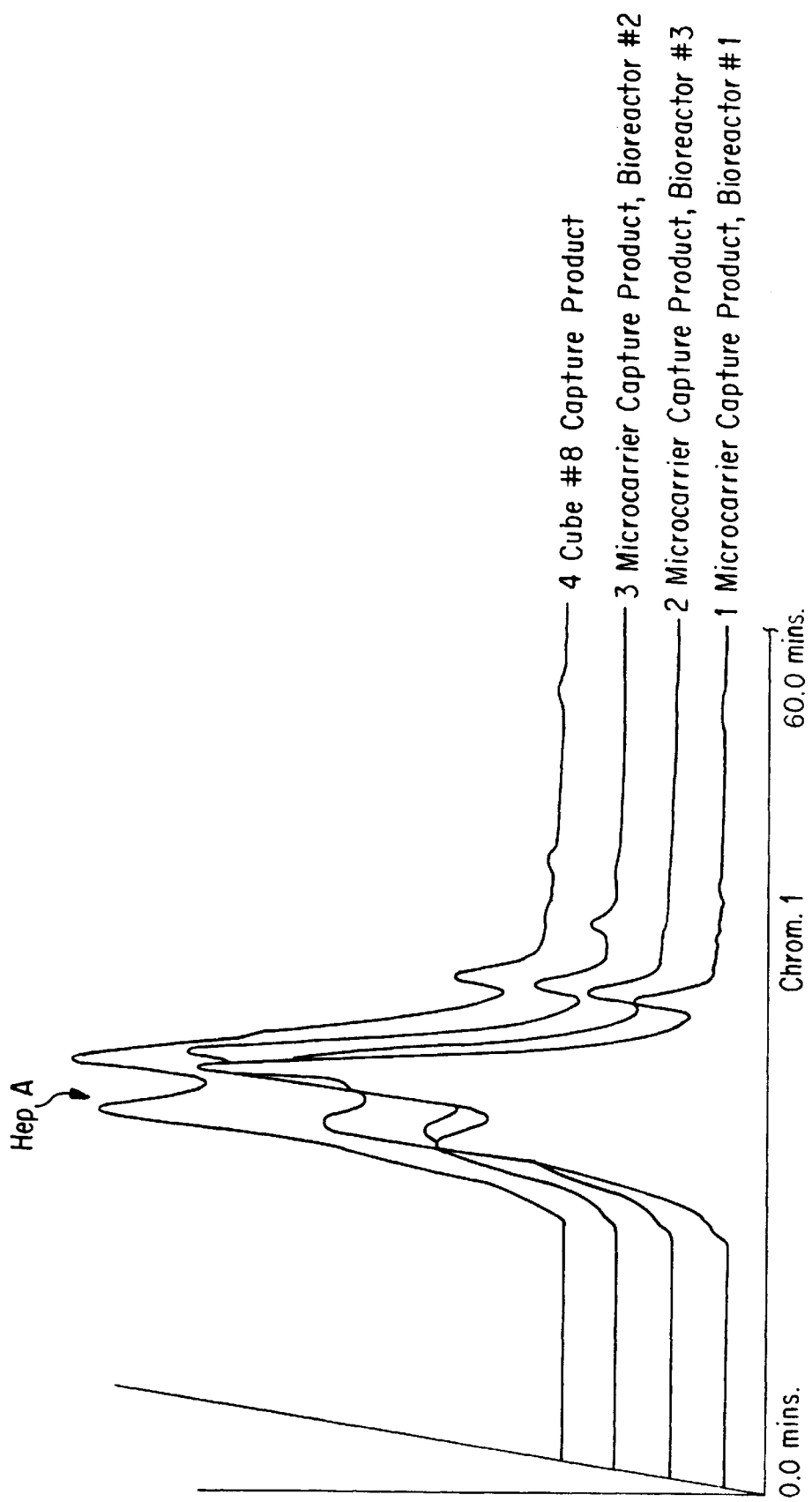
FIG. 13. HPSEC profiles at 260 mm for capture products from perfused microcarrier spinner cultures as compared with monolayer cell culture for hepatitis A virus grown on MRC-5 cells and SOLOHILL glass microcarriers, and COSTAR CUBE surfaces, respectively.
Figure 14:
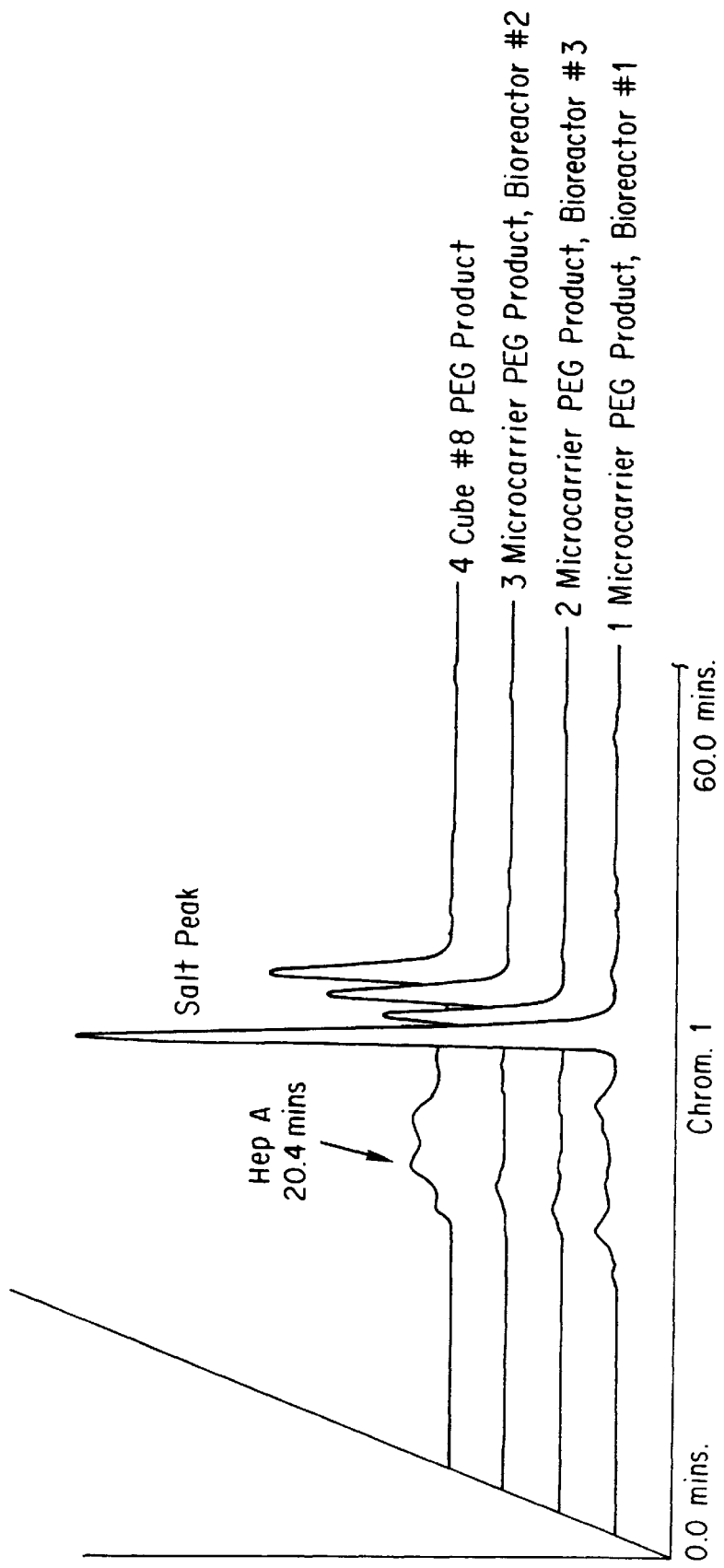
FIG. 14. HPSEC profiles at 260 mm for PEG precipitated product perfused microcarrier spinner cultures as compared with monolayer cell culture for hepatitis A virus grown on MRC-5 cells and SOLOHILL glass microcarriers, and COSTAR CUBE surfaces, respectively.
Figure 15:
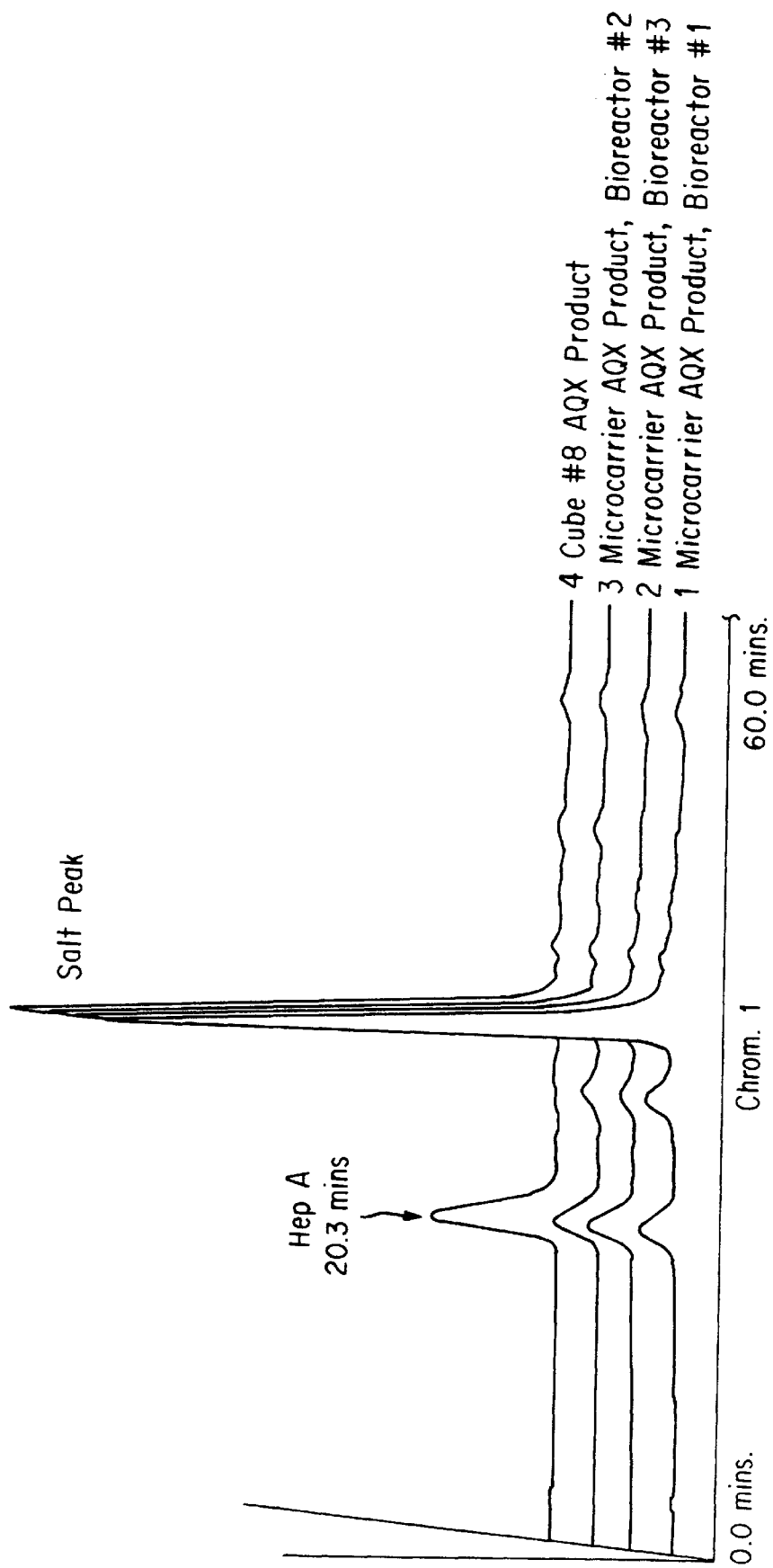
FIG. 15. HPSEC profiles at 260 mm for anion exchange product perfused microcarrier spinner cultures as compared with monolayer cell culture for hepatitis A virus grown on MRC-5 cells and SOLOHILL glass microcarriers, and COSTAR CUBE surfaces, respectively.

The objective of the purification work was to determine the difference between microcarrier derived lysate and lysate obtained from monolayer cell culture for subsequent purification. One liter of lysate from a COSTAR CUBE and approximately 800 ml of microcarrier lysate were purified side by side for comparitive purposes. The purification was carried through solvent extraction since a significant amount of purification is achieved by this point and should provide a good comparison of purification performance. Also, at this scale the amount of material to carry through the rest of the process was limited. As illustrated in Table 3, the EIA yields for the small scale process were in reasonable agreement with the full scale process. In addition, the microcarrier derived lysates yields were in excellent agreement with the production lysate control. A SDS PAGE silver strain run on the solvent extracted product, provided in FIG. 10, clearly indicates the 3 Hepatitis A bands for the small scale COSTAR CUBE lysate and the 3 microcarrier cultures. Another band does appear in the microcarrier lanes at about 66,000 molecular weight. This corresponds to BSA (66,200 MW) and is most likely derived from insufficient PBS washes during the harvest stage to remove serum proteins before the addition on the Triton Lysis Buffer. The COSTAR CUBE lysate had about twice the normal amount of Hep A by EIA normally seen in production, most likely due to inadequate mixing before sampling. The higher HAV content in the COSTAR CUBE lysate was carried through the process so that the difference in band density is due in part to this and in part to the ~50% yield from the MC cultures.

HPSEC profiles for the filtered lysate, nuclease treated lysate, capture product, PEG precipitate, and the solvent extraction are provided in FIGS. 11–15. Note that the profiles are very similar between the microcarrier and COSTAR CUBE lysate indicating similar purification performance for each input. In the solvent extracted profile the extra peak between the HAV and the solvent peak is believed to be the BSA band from the SDS PAGE gel. The relative % HAV areas for the PEG precipitate and solvent extracted product (AQX) are provided in Table 4. Note that the percent is calculated the same way as in production which accounts for all peaks before the solvent peak. Comparing the COSTAR CUBE #8 lysate to the microcarrier lysates shows relative agreement for the PEG product and a lower area % for the solvent extracted product. The extra peak in the microcarrier cultures is expected to be BSA. To account for this the HEPA area % were then recalculated by subtracting out the suspected BSA peak for comparison purposes. The relative area % for the microcarrier and COSTAR CUBE #8 lysates are in excellent agreement and show a surprisingly pure product at this point. Comparing the relative areas for COSTAR CUBE #8 lysate and the production COSTAR CUBE average shows slightly lower full scale yield for the PEG step and a much larger decrease for the solvent extraction step. This suggests a difference in the full scale and small scale purifications.

EXAMPLE 8

Propagation of Varicella Virus in Aggregated Microcarrier System

The following describes the infection of MRC-5 cells grown as an aggreagate culture with the Oka strain of Varicella virus.

Solohill glass coated microcarriers at 40 g/liter, 60 g/liter and 80 g/liter were prepared in a microcarrier spinner system as outlined in example 2 and inoculated with MCR-5 cells expansded in NUNC CELL FACTORIES in a similar manner as outlined in example 3. The cells were perfused at target rates of 1, 1.5, and 2 volumes per day and with the increasing rate corresponding to the higher bead loading. The perfusion operation was similar to example 4. Cells were grown for 4 to 5 days, at which time they were infected with working seed at approximately an infection ratio of 1 harvested working seed cell to 15 target cells in the microcarrier culture. The cell density at the time of infection varied from 2 to 4 million cells/ml. The working seed was prepared by infecting a ten layer NUNC CELL FACTORY with stockseed at an MOI of 1:125 and harvested with trypsin after 48 hours of infection. A sample of infected microcarrier culture was harvested at 6 hour time points starting at 30 hours by decanting off the media with four washes of phosphate buffered saline followed by resuspension in a stabilizer formation. The aggregates were broken up by fluid shear using a syringe needle. At approximately 48 hours post infection the entire volume of each of the three spinners was harvested using the fluid shear methodology described in example 6. The aggregates were more difficult to break up without the presence of detergent as described in example 6. Therefore, more fluid shear by increasing the linear velocity through the orifices is required.

EXAMPLE 9

Propagation of Mumps Virus in Aggreagated Microcarrier Culture

Either primary or cryopreserved Chick Embryo Fibroblast cells passaged multiple times in monolayer cultures, twice in this example, were added at about 5–10 cells per bead to microcarriers of different materials—glass coated plastic in this example—(diameter 150–212 $\mu$m, specific gravity 1.02) at 40 g/L in a 250 mL glass spinner vessel. A modified medium 199 or DMEM, with 10% FBS was used to grow the cells to a final density as high as $4\times10^6$ cells/mL with daily medium refeeds. The growth in this system was characterized by aggregation of microcarriers to progressively increasing size (2–50) as cell density increased. Infection and replication of mumps virus for the manufacture of the vaccine was demonstrated in this system by addition of Mumps virus seed (Jeryl Lynn Strain) to this microcarrier culture.

What is claimed is:

1. A method for producing large quantities of hepatitis A virus (HAV) in an aggregated microcarrier-cell culture which comprises retaining an HAV-infected MRC-5 cell population in an aggregated and attached state, with no observable floating MRC-5 cells due to cell sloughing from the microcarriers, comprising:

a) planting MRC-5 cells in a suitable culture medium at a planting concentration sufficient to achieve uniform attachment of the cells to glass coated microcarriers, such that essentially every microcarrier has at least one cell attached, b) growing the cells so attached to the microcarriers in a culturing vessel using a rate of agitation equal to the critical off bottom suspension rate, c) infecting the microcarrier aggregates in late log phase or early stationary phase with HAV, wherein said MRC-5 cells remain in an attached state, with no observable floating cells due to cell sloughing from the microcarriers, d) culturing the infected microcarrier-cell aggregates, and e) harvesting and recovering the HAV so produced.

2. The method of claim 1 wherein cells are planted at a density of about 5–10 cells per microcarrier.

3. The method of claim 2 wherein the microcarriers are glass coated polystyrene beads.

4. A method for producing large quantities of hepatitis A virus (HAV) in an aggregated microcarrier-cell culture which comprises retaining an HAV-infected MRC-5 cell population in an aggregated and attached state, with no observable floating MRC-5 cells due to cell sloughing from the microcarriers, comprising:

a) planting MRC-5 cells in a suitable culture medium at a planting concentration sufficient to achieve uniform attachment of the cells to glass coated microcarriers, such that essentially every microcarrier has at least one cell attached, b) growing the cells so attached to the microcarriers in a culturing vessel using a rate of agitation equal to the critical off bottom suspension rate, c) infecting the microcarrier aggregates in late log phase or early stationary phase with HAV, wherein said MRC-5 cells remain in an attached state, with no observable floating cells due to cell sloughing from the microcarriers, d) culturing the infected microcarrier-cell aggregates from about 14–28 days after infection, and e) harvesting and recovering the HAV so produced by forcing the aggregated microcarrier cell culture through a series of orifices of decreasing diameter such that the smallest orifice is approximately only twice the size of a single microcarrier.

5. The method of claim 4 wherein cells are planted at a density of about 5–10 cells per microcarrier.

6. The method of claim 5 wherein the microcarriers are glass coated polystyrene beads.

7. A method for producing large quantities of hepatitis A virus (HAV) in an aggregated microcarrier-cell culture which comprises retaining an HAV-infected MRC-5 cell population in an aggregated and attached state, without sloughing of MRC-5 cells from the microcarriers, comprising:

a) planting MRC-5 cells in a suitable culture medium at a planting concentration sufficient to achieve uniform attachment of the cells to glass coated microcarriers, such that essentially every microcarrier has at least one cell attached, b) growing the cells so attached to the microcarriers in a culturing vessel using a rate of agitation equal to the critical off bottom suspension rate, c) infecting the microcarrier aggregates in late log phase or early stationary phase with HAV, wherein said MRC-5 cells remain in an attached state, without sloughing from the microcarriers, d) culturing the infected microcarrier-cell aggregates, and e) harvesting and recovering the HAV so produced.

8. The method of claim 7 wherein cells are planted at a density of about 5–10 cells per microcarrier.

9. The method of claim 8 wherein the microcarriers are glass coated polystyrene beads.

10. A method for producing large quantities of hepatitis A virus (HAV) in an aggregated microcarrier-cell culture which comprises retaining an HAV-infected MRC-5 cell population in an aggregated and attached state, without sloughing of MRC-5 cells from the microcarriers, comprising:

a) planting MRC-5 cells in a suitable culture medium at a planting concentration sufficient to achieve uniform attachment of the cells to glass coated microcarriers, such that essentially every microcarrier has at least one cell attached, b) growing the cells so attached to the microcarriers in a culturing vessel using a rate of agitation equal to the critical off bottom suspension rate, c) infecting the microcarrier aggregates in late log phase or early stationary phase with HAV, wherein said MRC-5 cells remain in an attached state, without sloughing from the microcarriers, d) culturing the infected microcarrier-cell aggregates from about 14–28 days after infection, and e) harvesting and recovering the HAV so produced by forcing the aggregated microcarrier cell culture through a series of orifices of decreasing diameter such that the smallest orifice is approximately only twice the size of a single microcarrier.

11. The method of claim 10 wherein cells are planted at a density of about 5–10 cells per microcarrier.

12. The method of claim 11 wherein the microcarriers are glass coated polystyrene beads.

\* \* \* \* \*